(12) United States Patent
Leontein et al.

(10) Patent No.: US 11,497,838 B2
(45) Date of Patent: *Nov. 15, 2022

(54) IMMOBILISED BIOLOGICAL ENTITIES

(71) Applicant: W.L. Gore & Associates, Inc., Newark, DE (US)

(72) Inventors: Karin Leontein, Upplands Väsby (SE); Per Antoni, Upplands Väsby (SE); Daniel Nyström, Upplands Väsby (SE); Paul Begovac, Flagstaff, AZ (US); Krzysztof Pietrzak, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/914,085

(22) Filed: Jun. 26, 2020

(65) Prior Publication Data
US 2020/0324027 A1   Oct. 15, 2020

Related U.S. Application Data

(60) Continuation of application No. 15/684,007, filed on Aug. 23, 2017, now Pat. No. 10,736,999, which is a
(Continued)

(51) Int. Cl.
*A61L 33/00* (2006.01)
*A61P 7/02* (2006.01)
(Continued)

(52) U.S. Cl.
CPC ........... *A61L 33/0011* (2013.01); *A61L 27/34* (2013.01); *A61L 29/085* (2013.01); *A61L 31/10* (2013.01);
(Continued)

(58) Field of Classification Search
CPC ........ A61L 33/0011; A61L 27/34; A61I 31/10
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |

(Continued)

FOREIGN PATENT DOCUMENTS

| | | |
|---|---|---|
| EP | 0086186 A1 | 8/1983 |
| EP | 0086187 B1 | 10/1985 |

(Continued)

OTHER PUBLICATIONS

"Heparin", Wikipedia.com, 2012.
(Continued)

*Primary Examiner* — Lakshmi S Channavajjala

(57) ABSTRACT

There is described inter alia a device having a surface comprising a layered coating wherein the outer coating layer comprises a plurality of cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 and (iv) functional end groups, whereby one or more of said functional end groups have an anti-coagulant entity covalently attached thereto.

20 Claims, 7 Drawing Sheets

Related U.S. Application Data continuation of application No. 15/204,128, filed on Jul. 7, 2016, now Pat. No. 9,764,068, which is a division of application No. 14/790,205, filed on Jul. 2, 2015, now Pat. No. 9,408,950, which is a division of application No. 13/416,880, filed on Mar. 9, 2012, now Pat. No. 9,101,696.

(60) Provisional application No. 61/451,732, filed on Mar. 11, 2011.

(51) Int. Cl.

| | | |
|---|---|---|
| *C08L 79/02* | (2006.01) | |
| *A61L 27/34* | (2006.01) | |
| *A61L 29/08* | (2006.01) | |
| *A61L 31/10* | (2006.01) | |
| *C08G 81/00* | (2006.01) | |
| *A61L 33/06* | (2006.01) | |
| *A61L 33/08* | (2006.01) | |

(52) U.S. Cl.
CPC ....... *A61L 33/0035* (2013.01); *A61L 33/0064* (2013.01); *A61L 33/0076* (2013.01); *A61L 33/068* (2013.01); *A61L 33/08* (2013.01); *C08G 81/00* (2013.01); *A61L 2300/42* (2013.01); *A61L 2300/452* (2013.01); *Y10T 428/31971* (2015.04)

(56) References Cited

U.S. PATENT DOCUMENTS

| | | | |
|---|---|---|---|
| 4,326,532 A | 4/1982 | Hammar | |
| 4,329,383 A | 5/1982 | Joh | |
| 4,415,490 A | 11/1983 | Joh | |
| 4,526,714 A | 7/1985 | Feijen et al. | |
| 4,565,740 A | 1/1986 | Goelander et al. | |
| 4,600,652 A | 7/1986 | Solomon et al. | |
| 4,613,665 A | 9/1986 | Larm | |
| 4,678,671 A | 7/1987 | Feijen et al. | |
| 4,745,180 A | 5/1988 | Moreland et al. | |
| 4,810,784 A | 3/1989 | Larm | |
| 4,944,767 A | 7/1990 | Barbucci et al. | |
| 5,032,666 A | 7/1991 | Hu et al. | |
| 5,049,403 A | 9/1991 | Larm et al. | |
| 5,130,143 A | 7/1992 | Strickland et al. | |
| 5,213,898 A | 5/1993 | Larm et al. | |
| 5,308,617 A | 5/1994 | Halluin | |
| 5,417,969 A | 5/1995 | Hsu et al. | |
| 5,476,666 A | 12/1995 | Rhee et al. | |
| 5,510,418 A | 4/1996 | Rhee et al. | |
| 5,527,524 A | 6/1996 | Tomalia et al. | |
| 5,529,986 A | 6/1996 | Larsson et al. | |
| 5,532,311 A | 7/1996 | Sirvio et al. | |
| 5,583,213 A | 12/1996 | Yafuso et al. | |
| 5,606,012 A | 2/1997 | Tanzi et al. | |
| 5,876,433 A | 3/1999 | Lunn | |
| 5,897,955 A | 4/1999 | Drumheller | |
| 5,914,182 A | 6/1999 | Drumheller | |
| 5,916,585 A | 6/1999 | Cook et al. | |
| 5,922,690 A | 7/1999 | Van et al. | |
| 6,096,525 A | 8/2000 | Patnaik | |
| 6,120,536 A | 9/2000 | Ding et al. | |
| 6,361,819 B1 | 3/2002 | Tedeschi et al. | |
| 6,406,687 B1 | 6/2002 | Luthra et al. | |
| 6,440,947 B1 | 8/2002 | Barron et al. | |
| 6,461,665 B1 | 10/2002 | Scholander | |
| 6,642,242 B2 | 11/2003 | Collis et al. | |
| 6,653,457 B1 | 11/2003 | Larm et al. | |
| 6,787,179 B2 | 9/2004 | Timm et al. | |
| 6,800,331 B2 | 10/2004 | Bilyk et al. | |
| 6,887,249 B1 | 5/2005 | Houser et al. | |
| 7,034,061 B1 * | 4/2006 | Luthra | C08F 220/28 424/78.18 |
| 7,045,585 B2 | 5/2006 | Berry et al. | |
| 7,641,682 B2 | 1/2010 | Palmaz et al. | |
| 7,736,687 B2 | 6/2010 | Sims et al. | |
| 9,101,696 B2 | 8/2015 | Leontein et al. | |
| 9,408,950 B2 * | 8/2016 | Leontein | A61P 7/02 |
| 9,764,068 B2 * | 9/2017 | Leontein | A61L 33/0076 |
| 10,736,999 B2 * | 8/2020 | Leontein | A61L 33/068 |
| 2001/0036932 A1 | 11/2001 | Cardin et al. | |
| 2001/0044654 A1 | 11/2001 | Chen et al. | |
| 2002/0004101 A1 | 1/2002 | Ding et al. | |
| 2002/0016308 A1 | 2/2002 | Lassila et al. | |
| 2002/0068183 A1 | 6/2002 | Huang et al. | |
| 2002/0146414 A1 | 10/2002 | Sakiyama-Elbert et al. | |
| 2003/0134132 A1 | 7/2003 | Winterton et al. | |
| 2003/0135195 A1 | 7/2003 | Jimenez et al. | |
| 2005/0018552 A1 | 1/2005 | Tomisawa | |
| 2005/0059068 A1 | 3/2005 | Huang et al. | |
| 2005/0220839 A1 | 10/2005 | Dewitt et al. | |
| 2005/0232971 A1 | 10/2005 | Hossainy et al. | |
| 2006/0204533 A1 | 9/2006 | Hsu et al. | |
| 2007/0098708 A1 | 5/2007 | Myette | |
| 2007/0212388 A1 | 9/2007 | Patravale et al. | |
| 2007/0264302 A1 | 11/2007 | Cleek et al. | |
| 2007/0264308 A1 | 11/2007 | Cleek et al. | |
| 2008/0267903 A1 | 10/2008 | Uchegbu et al. | |
| 2008/0279909 A1 | 11/2008 | Cleek et al. | |
| 2009/0274737 A1 | 11/2009 | Borck | |
| 2010/0028402 A1 | 2/2010 | Dobrovolskaia et al. | |
| 2010/0074938 A1 | 3/2010 | Oscarson et al. | |
| 2011/0223229 A1 | 9/2011 | Vestberg | |
| 2017/0368237 A1 | 12/2017 | Leontein et al. | |

FOREIGN PATENT DOCUMENTS

| | | |
|---|---|---|
| EP | 0495820 B1 | 5/1995 |
| EP | 0923953 A2 | 6/1999 |
| EP | 0956870 A1 | 11/1999 |
| EP | 1559434 A1 | 8/2005 |
| EP | 1916260 A1 | 4/2008 |
| JP | 54-084398 A | 7/1979 |
| JP | 2001-524555 A | 12/2001 |
| JP | 2003-512490 | 4/2003 |
| WO | 87/07156 A1 | 12/1987 |
| WO | 93/05793 A1 | 4/1993 |
| WO | 93/21257 A1 | 10/1993 |
| WO | 97/07834 A2 | 3/1997 |
| WO | 98/08552 A1 | 3/1998 |
| WO | 99/26983 A1 | 6/1999 |
| WO | 00/01843 A1 | 1/2000 |
| WO | 01/29118 A1 | 4/2001 |
| WO | 01/41827 A1 | 6/2001 |
| WO | 01/87375 A1 | 11/2001 |
| WO | 03/57270 A1 | 7/2003 |
| WO | 2005/018552 A2 | 3/2005 |
| WO | 2007/133699 A2 | 11/2007 |
| WO | 2008/063157 A2 | 5/2008 |
| WO | 2010/029189 A2 | 3/2010 |
| WO | 2014/001827 A2 | 1/2014 |

OTHER PUBLICATIONS

Andersson, et al., "Optimal heparin surface concentration and antithrombin binding capacity as evaluated with human non-anticogulated blood in vitro", J. Biomed. Mater. Res. A, 2003, 67(2): 458-466.

Aulenta et al., "Dendrimers: a new class of nanoscopic contains and delivery devices", European Polymer Journal, 2003, 39:1741-1771.

Bai et al. Dendrimers as a Carrier for Pulmonary Delivery of Enoxaparin, a Low-Molecular Weight Heparin. J. Pharmaceutical Sciences, 2007, vol. 96, issue 8, pp. 2090-2106.

Behzad F, Brenchley P. A Multiwell Format Assay for Heparanase. Analytical Biochemistry 320 (2003); 207-213.

Choay J. Biologic studies on chemically synthesized pentasaccharide and tetrasaccharide fragments. Seminars in Thrombosis and Hemostasis 1985; 11:81-85.

(56) References Cited

OTHER PUBLICATIONS

Chuang et al., "Regulation of polyurethane hemocompatibility and endothelialization by tethered hyaluronic acid oligosaccharides", Biomaterials, 2009, 30:5341-5351.
Faulkners, Pope S, Burton-Pye B. Lanthanide Comlexes for Luminescence Imaging Application. Applied Spectroscopy Reviews 40, 1-31 (2005).
Freudenberg U, Hermann A, Welzel P et al. A star-PEG-heparin hydrogel platform to aid cell replacement therapies for neurodegenerative diseases. Biomaterials 2009; 30: 5049-5060.
Gavalas VG, Chaniotakis NA, Gibson TD. Improved operational stability of biosensors based on enzyme-polyelectrolyte complex adsorbed into a porous carbon electrode. Biosensors & Bioelectronics 1998;13:1205-1211.
Gibson TD, Pierce BLJ, Parker SM. Stabilisation of the Biological component of Biosensors. Biosensors for Food Analysis 1998; 46-53.
Griffith M. Heparin-catalyzed inhibitor/protease reactions: Kinetic evidence for a common mechanism of action of heparin. Proc. Natl. Acad. Sci. 1983; 80:5460-5464.
Hardhammar, PA, van Beusekom HMM, Emanuelsson HU, et al. Reduction in Thrombotic Events With Heparin-Coated Palmaz-Schatz Stents in Normal Porcine Coronary Arteries Circulation 1996; v93 n2:423-430.
Hellstrom WJG, Hyun JS, Human L, Sanabria JA, Bivalacqua TJ, Leungwattanakij S. Antimicrobial activity of antibiotic-soaked, Resist.TM.-coated Bioflex.RTM . . . International Journal of Impotence Research 2003; vol. 15, No. 1, p. 18-21.
Hermanson, Bioconjugate Techniques, ISBN: 978-0-12-370501-3, Bioconjugate Techniques, 2nd ed., 2008.
Hinrichs WLJ, ten Hoopen HWM, Wissink MJB, Engbers GHM, Feijen J. (1997) Design of a new type of coating for the controlled release of heparin Journal of Controlled Release, vol. 45, p. 163-176.
Homer A. Molecular-size-dependent variations in the proportions of chains with high binding affinities for antithrombin in rat skin heparin proteoglycans. Biochem J. 1989; 262:953-958.
Kadir,A. Saccharide sensing using gold and silver nanoparticles—A review. Journal of Fluorescence. 2004;14:391-400.
Klement P, Du Y, Berry L et al. Blood-compatible biomaterials by surface coating with a novel antithrombin-heparin covalent complex. Biomaterials 2002; 23;527-535.
Lam L, Silbert J, Rosenberg R. The separation of active and inactive forms of heparin. Biochem. Biophys. Res. Comm. 1976; 69:570-577.
Larsen, M.L. et al., Assay of Plasma Heparin Using Thrombin and the Chromogenic Substrate H—D—Phe—Pip—Arg—pNA (S-2238) Thromb Res 1978; 13:285-288.
Leclerc G. Drug Delivery from PC-Coated Cardiology Stents. Japanese Journal of Interventional Cardiology 2001; vol. 16, No. Suppl. 1, p. 107.
Letourneur D, Machy D, Pelle A, Marcon-Bachari E, D'Angelo G, Vogel M, Chaubet F, Michel JB. Heparin and non-heparin-like dextrans differentially modulate endothelial cell proliferation: In vitro evaluation with soluble and crosslinked polysaccharide matrices. Journal of Biomedical Materials Research 2002; vol. 60, No. 1, p. 94-100.
Lim JM, Do Y, Kim J. Synthesis, Structure and Magnetic Properties of Mn12 Single Molecule Magnet Containing 4-(Methylthio)benzoate as Peripheral Ligands. Bulletin of the Korean Chemical Society (2005); vol. 26, No. 7, p. 1065-1070.
Lin PH, Bush RL, Yao Q, Lumsden AA, Chen C. Evaluation of Platelet Deposition and Neointimal Hyperplasia of Heparin-Coated Small-Caliber ePTFE Grafts in a Canine Femoral Artery Bypass Model. Journal of Surgical Research 2004; vol. 118, No. 1, p. 45-52.
Lin PH, Chen C, Bush RL, Yao Q, Lumsden AB, Hanson SR. Small-caliber heparin-coated ePTFE grafts reduce platelet deposition and neointimal hyperplasia in a baboon model. Journal of Vascular Surgery 2004; vol. 39, No. 6, p. 1322-1328.
Lin PH, Chronos NA, Marijianowski MM, Chen C, et al. Heparin-coated Balloon-expandable Stent Reduces Intimal Hyperplasia in the Iliac Artery in Baboons J Vasc Intery Radial 2003; 14:603-611.
Linhardt RJ, Turnbull JE, Wang HM, Loganathan D, Gallagher T. (1990) Examination of the Substrate Specificity of Heparin and Heparin Sulfate Lyases Biochemistry, vol. 29, p. 2611-2617.
MacIntosh F. A colorimetric method for the standardization of heparin preparations. Biochem. 1941; 35:776-782.
Mulloy B, Forster, M. Conformation and dynamics of heparin and heparan sulfate. Glycobiology 2000; 10:1147-1156.
Nakajima M, Irimura T, Nicolson G. A Solid-Phase Substrate of Heparanase: Its Application to Assay of Human Melanoma for Heparan Sulfate Degradative Activity Analytical Biochemistry 157, 162-171 (1986).
Oliveira G, Carvalho L, Silva M. Properties of carbodiimide treated heparin. Biomaterials 2003; 24:4777-4783.
Park KD, Kim YS, Han DK, Kim YH, Lee EHB, Suh H, Choi KS. Bacterial adhesion on PEG modified polyurethane surfaces Biomaterials 1998; vol. 19, No. 7-9, p. 851-859.
Pasche B, Elgue G, Olsson P et al. Binding of antithrombin to immobilized heparin under varying flow conditions. Artif. Organs 1991;15:481-491.
Pedron et al. (Acta Biomaterialia 2010, vol. 6, Issue 11, pp. 4189-4198—Synthesis and characterization of degradable bioconjugated hydrogels with hyperbranched multifunctional cross-linkers).
Prakash et al., "Click modification of silica surfaces and glass microfluidic channels", Analytical Chemistry, 2007, 79(4):1661-1667.
Rocchietti S, Ubiali D, Terreni M, et al. Immobilization and Stabilization of Recombinant Mulitmeric Uridine and Purine Nucleoside Phosphorylases from Bacillus subtilis. Biomacromolecules 2004; 5:2195-2200.
Rosenberg R, Jordan R, Favreau L et al. Highly active heparin species with multiple binding sites for antithrombin. Biochem. Biophys. Res. Comm 1979; 86:1319-1324.
Salu KJ, Bosmans JM, Bult H, Vrints CJ. Drug-eluting stents: a new treatment in the prevention of restenosis Part I: experimental studies. Acta Cardiologica 2004; vol. 59, No. 1, p. 51-61.
Sanchez, et al., "Inhibition of the plasma contact activation system of immobilized heparin: relation to surface density of functional antithrombin binding sites", J. Biomed. Mater. Res., 1997, 37(1): 37-42.
Shou H, Ye J, Yu Q. Luminescence Properties of Benzoic Acid-Terbium Complexes. Journal of Luminescence (1988) vol. 42, p. 29-34.
Smith, et al., "Qantitation of glycosaminoglycan hexosamine using 3-methyl-2-benzothiazolone hydrazone hydrochloride", Anal. Biochem., 1979, 98: 478-480.
Tanzi M. Bioactive technologies for hemocompatibility. Expert Rev. Med. Devices 2005; 2:473-492.
Tomalia, "Dendrimers as building blocks for nanoscale synthesis", Aldrichimica Acta, 2004, 37(2): 1-52.
Yamaguchi N, Kiick K. Polysaccharide-poly(ethylene glycol) star copolymer as a scaffold for the production of bioactive hydrogels. Biomacromolecules 2005; 6:1921-1930.

* cited by examiner

IMMOBILISED BIOLOGICAL ENTITIES

REFERENCE TO RELATED APPLICATIONS

The present application is a continuation of U.S. Ser. No. 15/684,007 filed Aug. 23, 2017, which is a continuation of U.S. Ser. No. 15/204,128, filed Jul. 7, 2016, now U.S. Pat. No. 9,764,068, issued Sep. 19, 2017, which is a divisional of U.S. Ser. No. 14/790,205, filed Jul. 2, 2015, now U.S. Pat. No. 9,408,950, issued Aug. 9, 2016, which is a divisional of U.S. Ser. No. 13/416,880, filed Mar. 9, 2012, now U.S. Pat. No. 9,101,696, issued Aug. 11, 2015, that claims the benefit under 35 U.S.C. § 119 of U.S. Provisional Application Ser. No. 61/451,732, filed Mar. 11, 2011. The contents of all applications are herein incorporated by reference in their entireties.

This invention relates to immobilised biological entities to devices having surface coatings comprising such entities, and processes and intermediates for their production. In particular, the invention relates to immobilised anti-coagulant entities such as heparin and to devices, for example medical, analytical and separation devices having surface coatings comprising immobilised heparin.

BACKGROUND OF THE INVENTION

When a medical device is placed in the body, or in contact with body fluids, a number of different reactions are set into motion, some of them resulting in the coagulation of the blood in contact with the device surface. In order to counteract this serious adverse effect, the well-known anti-coagulant compound heparin has for a long time been administered systemically to patients before the medical device is placed in their body, or when it is in contact with their body fluids, in order to provide an antithrombotic effect.

Thrombin is one of several coagulation factors, all of which work together to result in the formation of thrombi at a surface in contact with the blood. Antithrombin (also known as antithrombin III) ("AT" or "ATIII") is the most prominent coagulation inhibitor. It neutralizes the action of thrombin and other coagulation factors and thus restricts or limits blood coagulation. Heparin dramatically enhances the rate at which antithrombin inhibits coagulation factors.

However, systemic treatment with high doses of heparin is often associated with serious side-effects of which bleeding is the predominant. Another rare, but serious complication of heparin therapy is the development of an immunological response called heparin induced thrombocytopenia (HIT) that may lead to thrombosis (both venous and arterial). High dose systemic heparin treatment e.g. during surgery also requires frequent monitoring of the activated clotting time (used to monitor and guide heparin therapy) and the corresponding dose adjustments as necessary.

Therefore solutions have been sought where the need for a systemic heparinisation of the patient would be unnecessary or can be limited. It was thought that this could be achieved through a surface modification of the medical devices using the anti-coagulant properties of heparin. Thus a number of more or less successful technologies have been developed where a layer of heparin is attached to the surface of the medical device seeking thereby to render the surface non-thrombogenic. For devices where long term bioactivity is required, the heparin layer should desirably be resistant to leaching and degradation.

Heparin is a polysaccharide carrying negatively charged sulfate and carboxylic acid groups on the saccharide units. Ionic binding of heparin to polycationic surfaces has been attempted, but these surface modifications tended to suffer from lack of stability over time resulting in lack of non-thrombogenic function, as the heparin leached from the surface.

Thereafter different surface modifications have been prepared wherein the heparin has been covalently bound to groups on the surface.

One of the most successful processes for rendering a medical device non-thrombogenic has been the covalent binding of a heparin fragment to a modified surface of the device. The general method and improvements thereof are described in European patents: EP-B-0086186, EP-B-0086187, EP-B-0495820 and U.S. Pat. No. 6,461,665.

These patents describe the preparation of surface modified substrates by first, a selective cleavage of the heparin polysaccharide chain, e.g. using nitrous acid degradation, leading to the formation of terminal aldehyde groups. Secondly, the introduction of one or more surface modifying layers carrying primary amino groups on the surface of the medical device, and thereafter reacting the aldehyde groups on the polysaccharide chain with the amino groups on the surface modifying layers followed by a reduction of the intermediate Schiff's bases to form stable secondary amine bonds.

Other methods of modifying surfaces are known. For example, US 2005/0059068 relates to a substrate for use in microassays. An activated polyamine dendrimer is covalently bonded to the surface of the substrate through a silane containing moiety. The dendrimer has branch points which are tertiary amines and terminal residues which are $NH_2$, OH, COOH or SH groups. Molecules containing OH or $NH_2$ functional groups can be bound to the dendrimer via the terminal residues of the dendrimer. Since the substrate is for use in microassays, it is usually a slide, bead, well plate, membrane etc. and the moiety containing the OH or $NH_2$ group is a nucleic acid, protein or peptide.

WO 03/057270 describes a device, for example a contact lens, with a lubricious coating having high surface hydrophilicity. A number of examples of coating materials are given including glycosaminoglycans (e.g. heparin or chondroitin sulfate) and PAMAM dendrimers. PAMAM dendrimers are said to be among the preferred coatings. The document exemplifies a contact lens having multiple layers of PAMAM dendrimer and polyacrylamide-co-polyacrylic acid copolymer (PAAm-co-PAA). The coating is formed by consecutively dipping the contact lens into solutions of the two coating materials, with the outer layer being PAAm-co-PAA.

US 2003/0135195 teaches a medical device such as a catheter with a highly lubricious hydrophilic coating formed from a mixture of colloidal aliphatic polyurethane polymer, an aqueous dilution of poly(l-vinylpyrrolidone-co-2-dimethylaminoethylmethacrylate)-PVP and dendrimers. The document teaches that the coating may be applied to the device by dipping the device in a colloidal dispersion of the aliphatic polyurethane polymer in a solution of poly(l-vinylpyrrolidone-co-2-dimethylaminoethylmethacrylate)-PVP and an active agent (e.g. heparin) in a mixture of dendrimer, water, N-methyl-2-pyrrolidone and triethylamine. The document teaches that heparin may be contained in the voids within the dendrimers. The document also teaches that the loaded heparin will elute from the hydrophilic polymer matrix at a predetermined rate.

US 2009/0274737 teaches implants such as stents having a hydrophilic surface with a wetting angle of ≤80°. There may be one, two or more anti-coagulant ingredients permanently bound to the surface and examples of anticoagulants include heparin and certain dendrimers, especially sulphated dendrimers. The surface may be functionalised in order to bind the anticoagulant and examples of functionalization are silanization and reaction with 1,1'-carbonyldiimidazole (CDI).

U.S. Pat. No. 4,944,767 relates to a polymeric material which is able to adsorb high quantities of heparin. The material is a block copolymer in which polyurethane chains are interconnected with polyamidoamine chains.

Our earlier application WO 2010/029189 relates to a medical device having a coating with an anticoagulant molecule such as heparin covalently attached to the coating via a 1,2,3-triazole linkage. The document describes the azide or alkyne functionalisation of a polyamine; the preparation of alkyne or azide functionalised heparin (both native and nitrous acid degraded heparin); and the reaction to link the derivatised heparin to the derivatised polymer via a 1,2,3-triazole linker.

The product described in WO 2010/029189 has many advantages but we have sought to develop an improved material in which the bioavailability of the heparin or other attached anti-coagulant molecule is increased, which may have greater stability on aging and which can be manufactured by a process which is robust and produces a product of high consistency.

Heparins have the ability to bind a wide variety of biomolecules including enzymes, serine protease inhibitors (such as antithrombin), growth factors and extracellular matrix proteins, DNA modification enzymes and hormone receptors. If used in chromatography, heparin is not only an affinity ligand but also an ion exchanger with high charge density. Thus biomolecules can be specifically and reversibly adsorbed by heparins immobilized on an insoluble support. Immobilised heparins therefore have a number of useful non-medical applications, particularly for analysis and separation.

SUMMARY OF THE INVENTION

According to the invention we provide, inter alia, a device having a surface comprising a layered coating wherein the outer coating layer comprises a plurality of cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anti-coagulant entity covalently attached thereto.

BRIEF DESCRIPTION OF THE FIGURES

In FIG. 9; plate A: Before; plate B: After.

DETAILED DESCRIPTION OF THE INVENTION

Anti-Coagulant Entities

Figure 1:
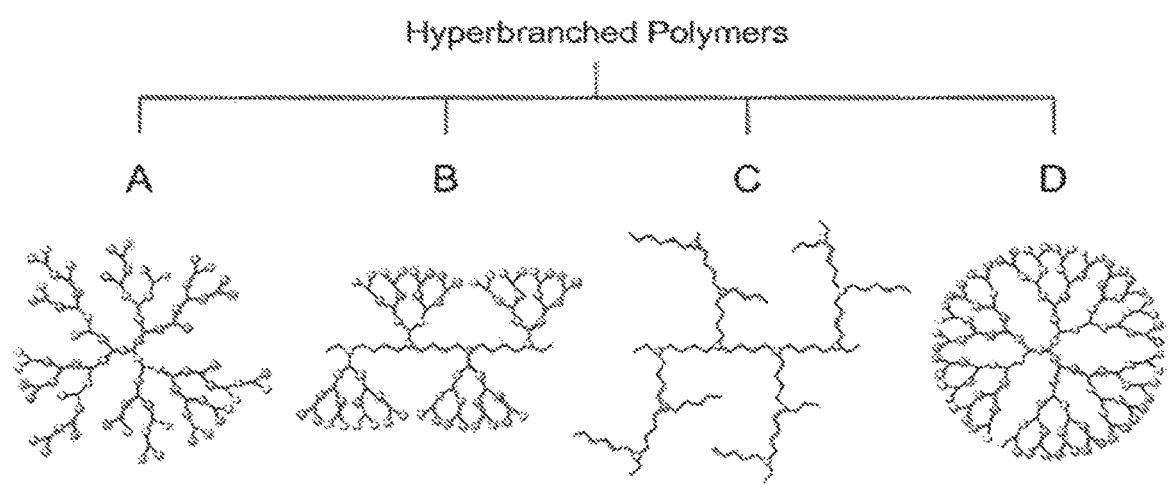
FIG. 1 is a schematic representation in 2-D of different types of hyperbranched polymers in which A represents a polymer with branching points (theoretically) in every monomeric unit; B represents a branched polymer with linear backbone and branched wedges, called dendrons, attached to it; C represents a polymer with branching units incorporated into linear segments; and D represents a dendrimer.

An anti-coagulant entity is an entity capable of interacting with mammalian blood to prevent coagulation or thrombus formation.

Anti-coagulant entities are well known to those skilled in the art and many of them are oligosaccharides or polysaccharides. Some of the entities are glycosaminoglycans including compounds containing glucosamine, galactosamine, and/or uronic acid. Among the most suitable glycosaminoglycans are "heparin moieties" and especially full length heparin (i.e. native heparin).

The term "heparin moiety" refers to a heparin molecule, a fragment of the heparin molecule, or a derivative or analogue of heparin. Heparin derivatives can be any functional or structural variation of heparin. Representative variations include alkali metal or alkaline earth metal salts of heparin, such as sodium heparin (e.g. Hepsal or Pularin), potassium heparin (e.g. Clarin), lithium heparin, calcium heparin (e.g. Calciparine), magnesium heparin (e.g. Cutheparine), and low molecular weight heparin (prepared by e.g. oxidative depolymerization or deaminative cleavage, e.g. Ardeparin sodium or Dalteparin). Other examples include heparan sulfate, heparinoids, heparin based compounds and heparin having a hydrophobic counter-ion. Other desirable anti-coagulant entities include synthetic heparin compositions referred to as "fondaparinux" compositions (e.g. Arixtra from GlaxoSmithKline) involving antithrombin-mediated inhibition of factor Xa. Additional derivatives of heparin include heparins and heparin moieties modified by means of e.g. mild nitrous acid degradation (U.S. Pat. No. 4,613,665) or periodate oxidation (U.S. Pat.

No. 6,653,457) and other modification reactions known in the art where the bioactivity of the heparin moiety is preserved.

Heparin moieties also include such moieties bound to a linker or spacer as described below. De-sulphated heparin, or heparin functionalized via e.g. the carboxylic acid group of the uronic acid moiety, are less suitable than other forms of heparin because of their generally reduced anti-coagulant properties relative to other forms of heparin. Mono-functionalization or low functionalization degrees of carboxylic acid groups can be acceptable as long as heparin bioactivity is preserved.

Suitably, each anti-coagulant entity is single point attached to a hyperbranched polymer molecule, particularly end point attached. The attachment is via functional end groups on the hyperbranched polymer molecule as discussed below. When the anti-coagulant entity is an end point attached heparin moiety, it is suitably connected to the hyperbranched polymer molecule through its reducing end (sometimes referred to as position C1 of the reducing terminal). The advantage of end point attachment, especially reducing end point attachment, is that the biological activity of the anti-coagulant entity (for example the heparin moiety) is maximized due to enhanced availability of the antithrombin interaction sites as compared with attachment elsewhere in the anti-coagulant entity (e.g. heparin moiety).

Where there is a multiplicity of anti-coagulant entities e.g. heparin moieties it is possible for some or all of them to be of a different type; however generally they will all be of the same type.

Anti-coagulant entities are commonly anionic (as in the case of heparin moieties).

Other anti-coagulant entities such as hirudin, coumadins (vitamin K antagonists of the 4-hydroxycoumarin class like warfarin), anti-platelet drugs (as clopidogrel and abciximab), argatroban, thrombomodulin or anti-coagulant proteins (like proteins C, S or antithrombin) may also be considered for use. Anti-coagulant entities may also include enzymes such as apyrase. Such substances may be charged (e.g. anionic) or uncharged. The way these may be attached to the hyperbranched polymer so that its bioactivity is preserved can be designed by someone skilled in the art.

Hyperbranched Polymers

Examples of various types of hyperbranched polymers are shown schematically in FIG. 1, types A to D. A, in FIG. 1, represents a polymer with branching points (theoretically) in every monomeric unit; B represents a branched polymer with linear backbone and branched wedges, called dendrons, attached to it; C represents a polymer with branching units incorporated into linear segments; and D represents a dendrimer. These polymers are examples of hyperbranched polymers useful in the context of the present invention if the core segment is sufficiently small in relation to the overall size of the molecule.

The term "hyperbranched polymer molecule" is well understood in the art to refer to a molecule having a tree like branching structure emanating from a core moiety typically in the centre. In the context of the present invention, the term also includes dendrimers, which are well known and are hyperbranched polymer molecules in which the degree of branching is 100% (occasionally referred to herein as "perfectly branched" i.e. 100% of functional groups capable of branching are branched) and which are therefore highly symmetrical about the core. Hyperbranched polymers consist of three basic architectural components, (i) the core, (ii) the interior and (iii) the functional end groups. The core is positioned at the centre of the molecule and to it branched wedges, called dendrons, are attached. The dendrons may be perfectly branched or less than perfectly branched.

The core of a hyperbranched polymer molecule is polyfunctional (either with several of the same type or several of different types of functionalities) and the number of functional groups it bears dictates the number of branches possible to be introduced in the molecule. Typically all functional groups of the core are utilized in branching. Similarly, the shape of a hyperbranched polymer molecule is determined by the core shape, with substantially tetrahedral cores giving rise to substantially spherical hyperbranched polymer molecules and more elongated cores giving rise to ovoid or rod-shaped hyperbranched polymer molecules.

According to the invention, the core moiety will be a relatively small entity in relation to the overall size of the polymer, having a molecular weight of between 14 and 1,000 Da, more usually between 40 and 300 Da and for example 50 to 130 Da.

Figure 2:
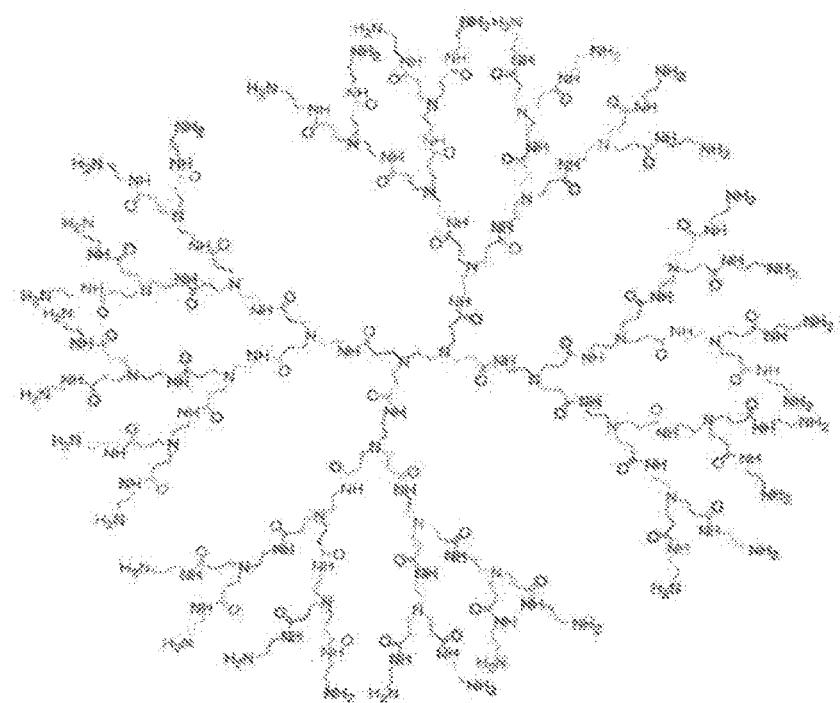
FIG. 2 illustrates in 2-D an exemplary PAMAM dendrimer having 3 generations (in 3-D the structure would be approximately spherical).
Figure 3:
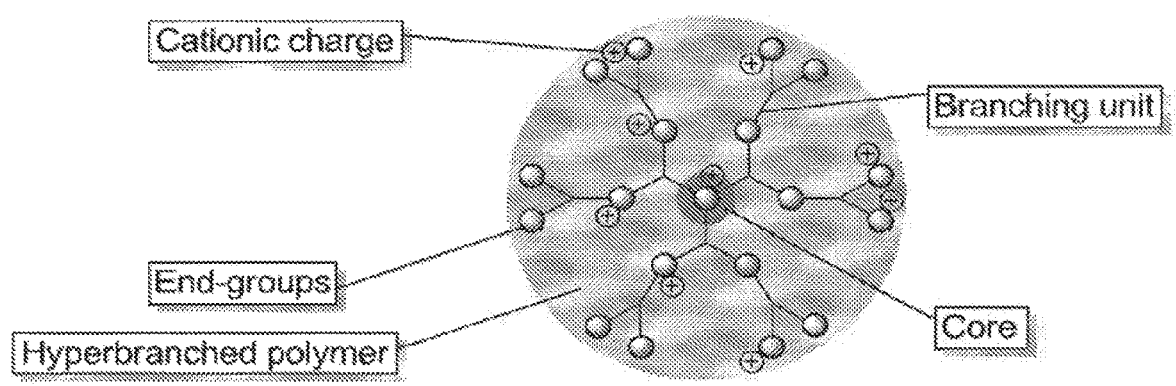
FIG. 3 is a schematic illustration in 2-D of an exemplary second generation dendrimer in which the core has three reactive functional groups, all of which are substituted; the first layer has six reactive functional groups, all of which are substituted; and the second layer has twelve reactive functional groups. Such a dendrimer will adopt a substantially spherical shape in 3-D.

Dendrimers are perfectly branched molecules in which the degree of branching is 100%, thus their structure is highly regular and therefore, for a given starting material, the only variable is the number of layers or generations in the dendrimer. The generations are conventionally numbered outwards from the core. See, for example, Tables 2-4 below. FIG. 2 illustrates a third generation dendrimer and FIG. 3 illustrates a second generation dendrimer. Because of their highly consistent and symmetrical structure, the molecular weight distribution for dendrimers of a given generation is extremely narrow, which is highly advantageous as it leads to a very consistent product.

Other hyperbranched molecules also contain a high number of branches, however, and, for example the degree of branching will usually be at least 30%, 40% or 50% for example at least 60%, 70%, 80% or 90%. Unlike dendrimers, the structure of such hyperbranched molecules will not be completely regular but they may also adopt a generally globular structure.

Typically the core is the moiety of a molecule which is not the same as the repeating unit(s) of the polymer. However in one embodiment the core is a moiety of the same type as the repeating unit (or one of the repeating units) of the polymer.

Hyperbranched polymer molecules are generally prepared either by employing a divergent method, in which the layers are built up from a core, or a convergent method in which fragments are built up and then condensed. Dendrimers are more usually prepared using the divergent method.

In the synthesis of dendrimers a high degree of control over the addition reaction of every branching unit is essential and the resulting products show a polydispersity index (PDI) between 1.00 and 1.05. The dendron size depends on the number of monomer layers and every added layer is represented by a generation (G). The interior consist of branching monomers that have ABx functionality where x≥2. Careful preparation of the branching unit makes it possible to control the reaction between A and B' if B' is the activated state of B. Larger dendrimers give rise to globular shaped, nanoscale sized, structures with low intrinsic viscosity as a result.

Traditionally, dendrimers are synthesized by employing an iterative technique where ABx monomers are alternately added to the growing species followed by an activation/deprotection step. These protocols depend on efficient reactions that ensure full substitution of the terminal groups B'. Any deviation will give structural defects that accumulate during dendrimer growth resulting in tedious or impossible purification procedures.

See Aldrichimica Acta (2004) 37(2)1-52 "Dendrimers: building blocks for nanoscale synthesis", herein incorporated in its entirety by reference, e.g. at pages 42-43 for further discussion of dendrimer synthesis and nomenclature.

Hyperbranched polymers which are dendrimers with structural defects of this type can be used in this invention.

Hyperbranched polymers which are not dendrimers may, for example, be formed by polymerization of a reactive monomer or more than one reactive monomer. For example hyperbranched polymers which are polyamines may be prepared by polymerization of aziridine for example by treatment with base.

Exemplarily core moieties include amines such as the moiety of ammonia (Mw 14 Da), diamines (e.g. ethylene diamine (Mw 56 Da), propylene diamine (Mw 70 Da) or 1,4-diaminobutane (Mw 84 Da)), and triamines (e.g. diethylenetriamine ($NCH_2CH_2NHCH_2CH_2N$) (Mw 99 Da) or 1,2,3-triaminopropane (89 Da)). Other cores may be oxygen containing including $C(Me)(CH_2O)_3$ (Mw 117 Da) or sulfur containing including ($NCH_2CH_2S$—$SCH_2CH_2N$) (Mw 148 Da).

Cationic hyperbranched polymers will have a predominantly positive charge at about pH 7 that is to say that they either contain only uncharged groups and charged groups having positive charge at pH 7 or else (less preferred) have groups that are negatively charged at pH 7 that are outnumbered by groups that are positively charged. Cationic hyperbranched polymers of this invention typically will have primary amines as functional end groups.

Hyperbranched polymers of use according to the invention may contain a number of functionalities for example they may be polyamines (entirely or substantially containing secondary and tertiary amine groups and with primary amines as functional end groups), polyamidoamines (amide groups and secondary and tertiary amine groups and with primary amines as functional end groups) or polyethers with amine functionality (e.g. polyethers such as PEGs in which end groups have been transformed into primary amine groups).

An exemplary family of hyperbranched polymers are the polyamidoamines (PAMAMs) in which a moeity of ammonia or a di- or tri-amine (e.g. ethylenediamine) may be used as the core moiety and the addition of generations of the branched molecule may be built up by reacting the ammonia or the free amine groups with e.g. methyl acrylate followed by ethylene diamine leading to a structure having a number of free amine groups on the outer surface. Subsequent generations can be built up by further reaction with methyl acrylate and ethylene diamine. A structure in which all primary amine groups of the inner layers have been reacted with methyl acrylate and ethylenediamine will be a dendrimer. PAMAM dendrimers are available under the trade mark Starburst®, manufactured by Dendritech Inc. Starburst dendrimers are sold by Dendritech Inc., Sigma Aldrich and Dendritic Nanotechnologies (DNT).

Other exemplary hyperbranched polymers may include polyamines such as polypropyleneimine (PPI) and polyethyleneimine (PEI) polymers formed by polymerization of the respective building blocks. Hyperbranched polymers based on PPI may also be synthesized from a core such as diaminobutane and built up by reaction of the primary amine groups with acrylonitrile followed by hydrogenation. PPI dendrimers are available under the trade mark Astramol™ and provided by DSM and Sigma Aldrich. Polyethyleneimine (PEI) polymers are available from e.g. BASF, Nippon Shokubai and Wuhan Bright Chemical.

Thus, the hyperbranched polymer may be selected from polyamidoamine, polypropyleneimine, polyethyleneimine and other polyamine polymers and copolymers comprising one or more of polyamidoamine, polypropyleneimine, polyethyleneimine and polyamine hyperbranched polymers.

In general, cationic hyperbranched polymers having primary amine groups as functional end groups, for example PAMAMs or polyethylenimines or polypropyleneimines, are particularly suitable for use in the present invention.

Hyperbranched aminated polymers comprising esters, carbonates, anhydrides and polyurethanes are less suitable as they tend to degrade. However, the biostability can depend on the number and proportion of biodegradable groups and some may therefore be suitable within this invention.

The properties of certain hyperbranched polymers are described in Table 1 below:

TABLE 1

Examples of hyperbranched polymers with appropriate ratio of total molecular weight to core moiety molecular weight

| Type | Supplier | Brand name | Core | Molecular weight [Da] | Ratio |
|---|---|---|---|---|---|
| PEI | BASF | Lupasol ® WF | Ethane-1,2-diamine (Mw 56 Da) | 25,000 | ~450:1 |
| PAMAM | Dendritech DNT Sigma Aldrich | Starburst ® G3-G10 | Ethane-1,2-diamine (Mw 56 Da) | 7,000-935,000 (e.g. 7,000-900,000) | ~125:1-16,700:1 |

TABLE 1-continued

| Type | Manufacturer | Brand name | Core | Molecular weight [Da] | Ratio |
|---|---|---|---|---|---|
| PPI | DSM Sigma Aldrich | Astramol ™ Am-64 | Butane-1,4-diamine (Mw 84 Da) | 7,000 | ~85:1 |
| PEI | Nippon Shokubai | Epomin-P-1050 | Ethane-1,2-diamine (Mw 56 Da) | 70,000 | ~1250:1 |
| PEI | Wuhan Bright Chemical | G-35 | Ethane-1,2-diamine (Mw 56 Da) | 70,000 | ~1250:1 |

Examples of polymers with other types of structure (not suitable hyperbranched polymers within the terms of the present invention)

| Type | Manufacturer | Brand name | Core | Molecular weight [Da] | Ratio |
|---|---|---|---|---|---|
| PEI | BASF | Lupasol ® SN | Undefined, polymeric | 1,000,000 | N/A |
| PEI | BASF | Lupasol ® SK | Undefined, polymeric | 2,000,000 | N/A |
| PEI | Wuhan Bright Chemical | G-35 | Ethane-1,2-diamine (Mw 56 Da) | 1,500 | ~25:1 |
| PAMAM | Dendritech DNT Sigma Aldrich | Starburst ® G1 | Ethane-1,2-diamine (Mw 56 Da) | 1,430 | ~26:1 |
| PPI | DSM | Astramol ™ Am-8 | Butane-1,4-diamine (Mw 84 Da) | 316 | ~4:1 |

The PAMAM illustrated in FIG. 2 is based on ethylenediamine as core moiety. The properties according to the number of generations built up are described in Table 2 below:

TABLE 2

| Generation | Mw (Da) | Measured diameter/ Angstrom | Number of surface groups | Ratio of Total Mw to core Mw |
|---|---|---|---|---|
| Core/G0 | 56/517* | 15 | 4 | ~9:1 |
| 1 | 1,430 | 22 | 8 | ~26:1 |
| 2 | 3,256 | 29 | 16 | ~58:1 |
| 3 | 6,909 | 36 | 32 | ~125:1 |
| 4 | 14,215 | 45 | 64 | ~250:1 |
| 5 | 28,826 | 54 | 128 | ~515:1 |
| 6 | 58,048 | 67 | 256 | ~1,040:1 |
| 7 | 116,493 | 81 | 512 | ~2,080:1 |
| 8 | 233,383 | 97 | 1,024 | ~4,170:1 |
| 9 | 467,162 | 114 | 2,048 | ~8,340:1 |
| 10 | 934,720 | 135 | 4,096 | ~16,700:1 |

See Aldrichimica Acta (2004) 37(2) 1-52 "Dendrimers: building blocks for nanoscale synthesis"
*Structure, see Scheme 1

Scheme 1. Synthesis of a PAMAM-G0 dendrimer. In Scheme 1: a is methyl acrylate and b is ethane-1,2-diamine.

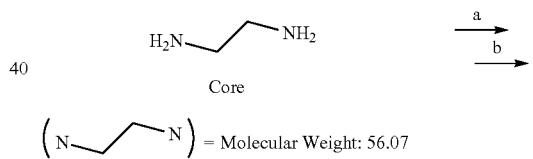

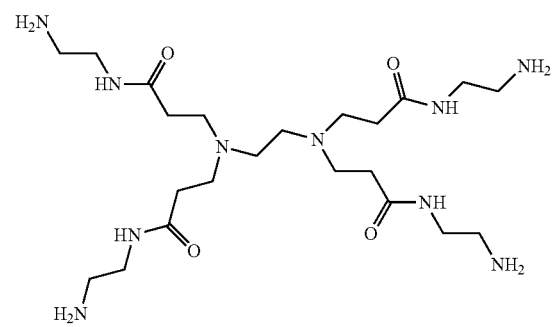

PAMAM-G0
Molecular Weight: 516.68

Synthesis of an exemplary PEI hyperbranched polymer based on ethylenediamine core by polymerization of aziridine is shown in Scheme 2.

Scheme 2.
Synthesis of a PEI hyperbranched polymer.

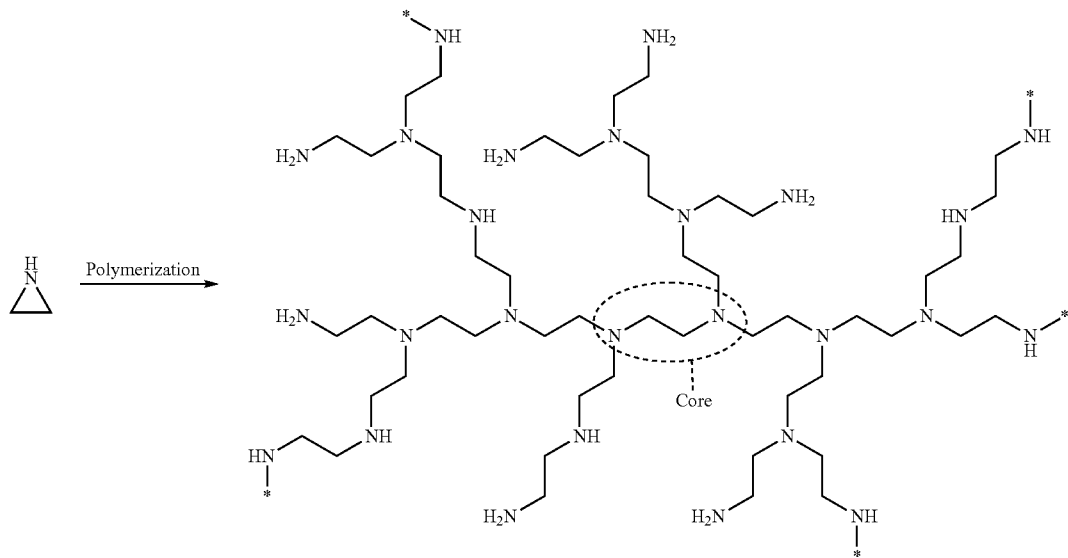

In Scheme 2: the PEI hyperbranched polymer is of the 4$^{th}$ generation having a ethane-1,2-diamine core (Mw = 56 Da).
*indicates exemplary positions where further aziridine monomers may be added.

Synthesis of an exemplary PPI dendrimer based on butane,1,4-diamine core by polymerization of acrylonitrile is shown in Scheme 3.

Scheme 3. Synthesis of PPI dendrimer. In Scheme 3: the ppo dendrimer is of the 3$^{rd}$ generation having a butane-1,4-diamine core (Mw = 84 Da).

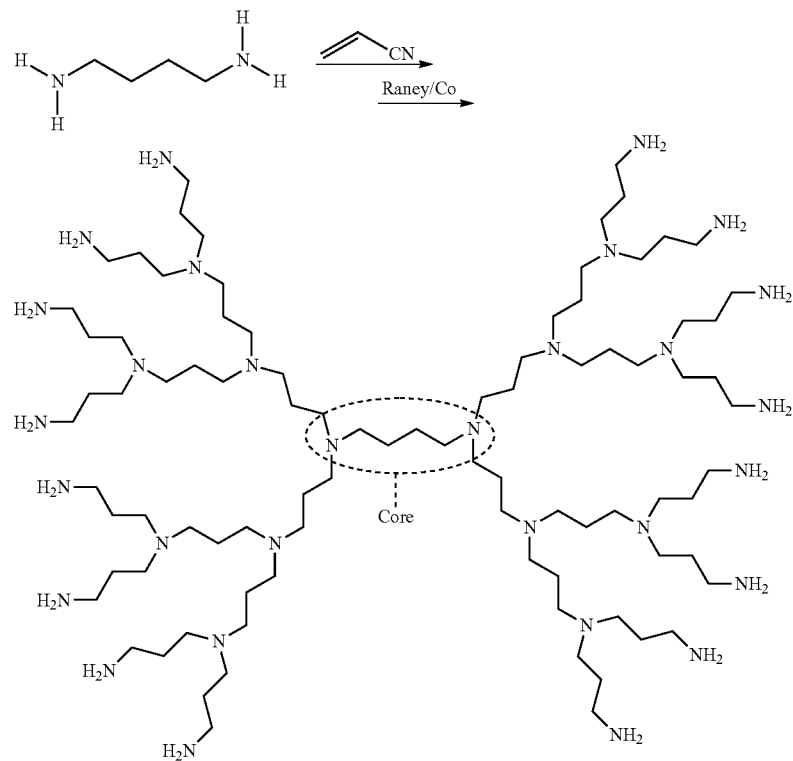

The hyperbranched polymer molecules useful in the present invention typically have a molecular weight of about 1,500 to 1,000,000 Da, more typically about 10,000 to 300,000 Da e.g. about 25,000 to 200,000 Da. The hyperbranched polymer molecules useful in the present invention suitably are substantially spherical in shape. Typically they have a diameter of about 2 to 100 nm, e.g. 2 to 30 nm, especially about 5 to 30 nm as determined by laser light scattering.

When the hyperbranched polymer is a PAMAM dendrimer, it typically has a molecular weight of about 5,000 to 1,000,000 Da, more typically about 12,000 to 125,000 Da and a diameter of about 1 to 20 nm, e.g. 2 to 10 nm, especially about 4 to 9 nm.

In hyperbranched polymers of use according to the invention the ratio of total molecular weight to core moiety molecular weight is at least 80:1, for example at least 100:1, for example at least 200:1 e.g. at least 500:1 e.g. at least 1000:1. The ratio is typically less than 20,000:1 e.g. less than 10,000:1 e.g. less than 5,000:1. For example the ratio is between 80:1 and 20,000:1 e.g. 200:1 and 5,000:1 e.g. between 200:1 and 1600:1 e.g. between 400:1 and 1600:1.

For the avoidance of doubt, the total molecular weight of the hyperbranched polymer referred to herein excludes the weight of any covalently attached anti-coagulant entity or any beneficial agent.

The ratio is dictated by the molecular weight of the core and the total molecular weight of the hyperbranched polymer. The calculated ratio will vary as the core varies (in terms of chemical composition and molecular weight) and as the molecular weight of the generations varies (in terms of molecular weight of monomers and number of monomers attached in each generation).

For PAMAM dendrimers a core derived from ethane-1, 2-diamine is preferred and the number of generations is preferably between 3 and 10, more preferably between 4 and 7 i.e. 4, 5, 6 or 7.

For PAMAM hyperbranched polymers, a core derived from ethylenediamine is preferred and the number of incorporated reactive monomers (methylacrylate, Mw=56 Da and ethylenediamine, Mw=57 Da) in the hyperbranched polymer is exemplarily between 50 and 9,000 e.g between 100 and 5,000 e.g. between 100 and 2,000 of each monomer.

For PEI hyperbranched polymers, a core derived from ethylenediamine is preferred and the number of incorporated aziridine monomers (Mw=42 Da) in the hyperbranched polymer is exemplarily between 110 and 20,000 e.g between 110 and 10,000 e.g. between 110 and 3,000 monomers.

For PPI hyperbranched polymers, a core derived from butane-1,4-diamine is preferred and the number of incorporated acrylonitrile monomers (Mw=56 Da) in the hyperbranched polymer is exemplarily between 120 and 17,000 e.g between 120 and 4,000 e.g. between 120 and 1,000 monomers.

Figure 5:
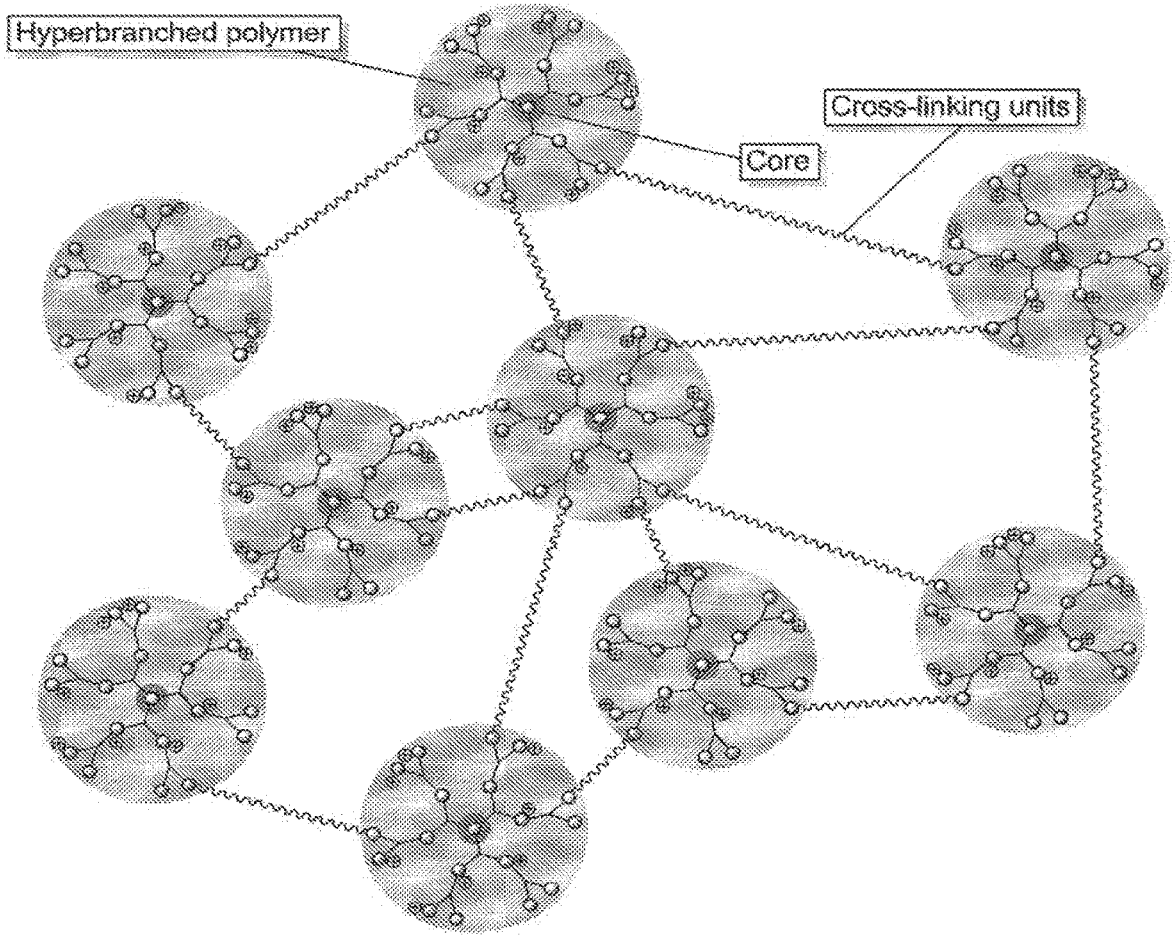
FIG. 5 shows how several dendrimers or other hyperbranched polymers may be cross-linked to each other prior to functionalisation by heparin or other anti-coagulant entity.
Figure 6:
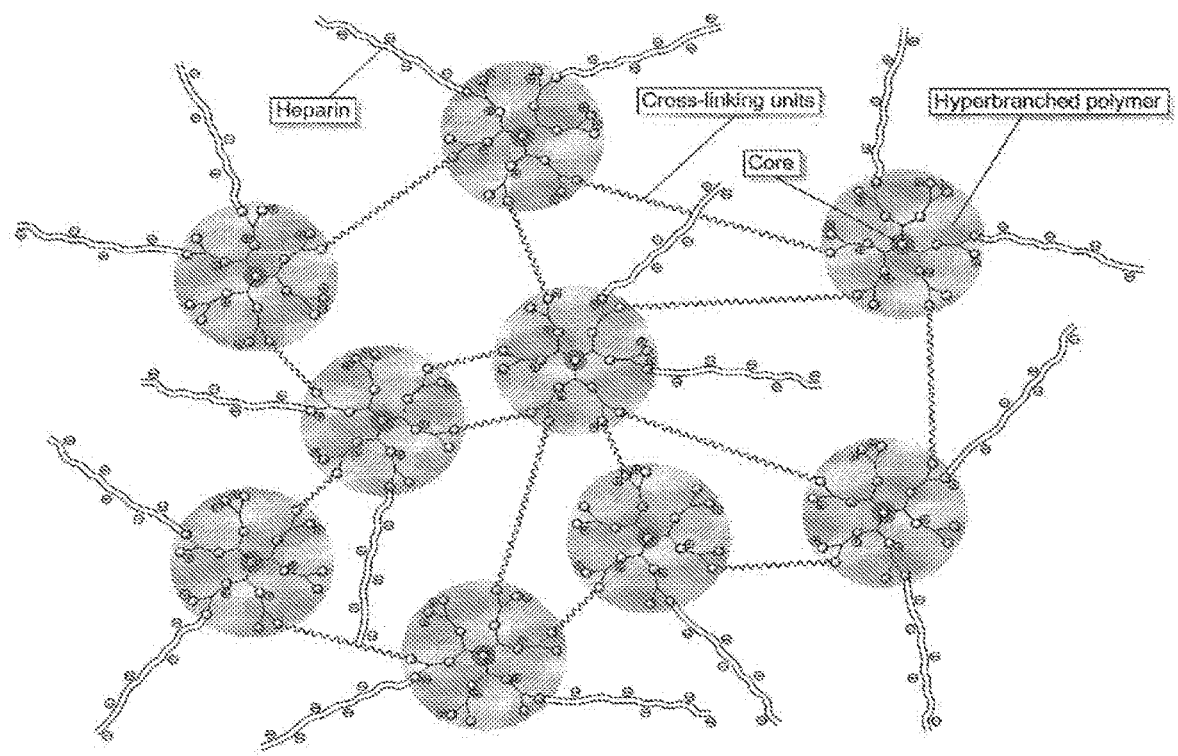
FIG. 6 shows how several dendrimers or other hyperbranched polymers which have been functionalised by heparin or other anti-coagulant entity may be cross-linked to each other.

In the device of the present invention, the plurality of cationic hyperbranched polymer molecules may optionally be cross-linked to one another on the surface of the device. Cross-linking may take place either before or after the hyperbranched polymer molecules are applied to the surface of the device and either before or after the anti-coagulant entities are attached thereto (see FIGS. 5, 6).

In the case where the hyperbranched polymer molecules are cross-linked, the number of molecules that may be cross-linked to form an aggregate hyperbranched polymer is two or more and, for example, from 2-500 e.g. from 2-10 such as from 2-5; and each molecule may be attached to another molecule in the aggregate by one or more cross-linkages e.g. up to 10 cross linkages.

Aggregates of 2 or more hyperbranched polymer molecules useful in the present invention typically have a molecular weight of about 3,000 to 2,000,000 Da, more typically about 50.000 to 500,000 Da. The hyperbranched polymer aggregates useful in the present invention typically have a diameter of about 5 to 100 nm, especially about 20 to 100 nm.

Derivatisation of Hyperbranched Polymer Molecules with Anti-Coagulant Entities

Figure 4:
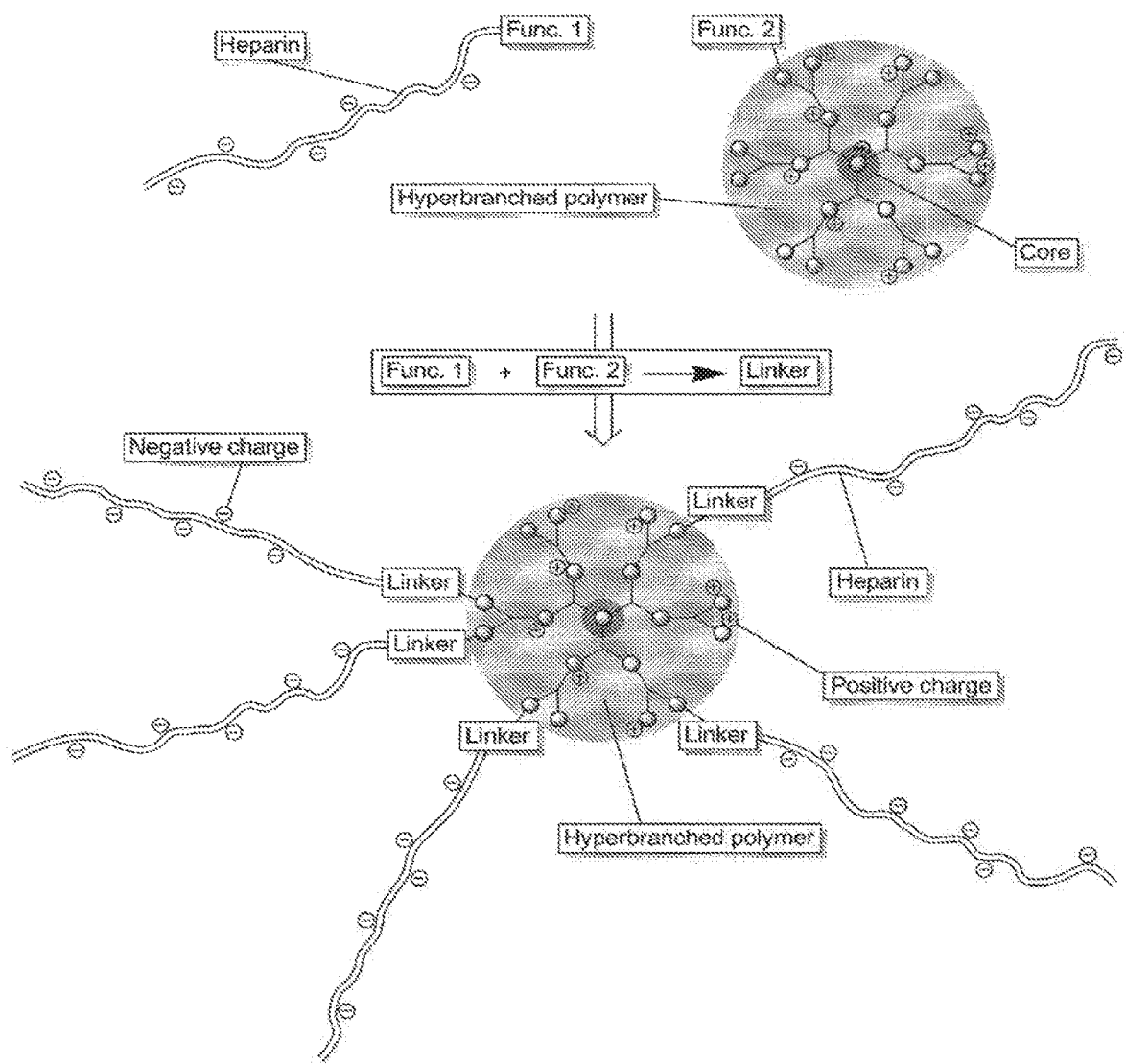
FIG. 4 illustrates how a first functional group on a heparin moiety (or other anti-coagulant entity) may be reacted with a second functional group which is an end group of the dendrimer or other hyperbranched polymer.

Hyperbranched polymer molecules have a large number of functional end groups which can be reacted with anti-coagulant entities such as heparin (see FIG. 4). The functional end groups can be of the same type or of several different types, as appropriate. Therefore, one of the advantages of the present invention is that it is possible to design the molecule such that it has a required number of functional end groups of a specific functionality. This makes it possible to selectively immobilize the desired amount of anti-coagulant entities on the surface of a device without interfering with the build up of the underlying layers.

The branching structure of the hyperbranched molecules makes it possible to obtain a higher surface density of anti-coagulant entities than was possible using essentially linear polymer structures, while still achieving sufficient spacing of those anti-coagulant entities to ensure that the bioavailability of each entity is not reduced in comparison with that achieved using previously known coatings and may actually be increased.

Another useful feature of hyperbranched polymers is that the majority of the reactive functional end groups are on the surface of the hyperbranched molecule and therefore substantially all of the anti-coagulant entity is available on the surface of the hyperbranched polymer. The effect is particularly marked in the case of dendrimers, where all of the available functional groups are on the surface. This feature gives a particular advantage over conventional coating polymers in which many of the reactive functional end groups may be hidden in the interior of the structure rather than on the surface. This means that anti-coagulant entity which reacts with functional groups in such conventional coating polymers may be immobilized in the interstices of the polymer surface and will not be bioavailable.

The derivatised hyperbranched polymer architecture will allow a more homogenous distribution of the anti-coagulant entity throughout the layers in which it is incorporated, such as the outer coating layer, which should, in principle, result in increased ageing stability. Further, the possibility of selecting and adjusting the anti-coagulant density on the hyperbranched polymer will allow for a more robust and predictable anti-coagulant distribution on the device. The pre-fabrication of the hyperbranched polymer-anti-coagulant entity conjugate also allows a lower batch to batch variability, since it is easier to adjust the degree of substitution of the hyperbranched polymer by the anti-coagulant entity (e.g. heparin) in solution rather than on a surface.

In a further aspect of the invention there is provided a cationic hyperbranched polymer molecule characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anti-coagulant entity covalently attached thereto.

Depending on the number of anti-coagulant entities attached to functional end groups, and their charge (e.g. negatively charged in the case of heparin as anti-coagulant entity), the cationic hyperbranched polymer may have a net positive or a net negative charge.

Suitably the anti-coagulant entity has a covalent connection only to a single functional end group on one hyperbranched polymer molecule and not to any other molecule. The coupling of the anti-coagulant entity is never to the core of the hyperbranched polymer, only to a functional end group of the hyperbranched polymer.

The number of functional end groups which have an anti-coagulant entity covalently attached thereto is one or more, for example 2 or more, for example 2 to 200 e.g. 10 to 100 however there is no specific upper limit. The number that may be attached will depend on the number of end groups that are available, which is a function of the size of the cationic hyperbranched polymer molecule. The number of functional end groups which have an anti-coagulant entity covalently attached thereto may for example be 1 to 95% e.g. 5 to 95% e.g. 10 to 80% e.g. 10 to 50% of available functional end groups. The number of functional end groups which have an anti-coagulant entity covalently attached thereto may for example be 5 to 50% e.g. 5 to 40% e.g. 5 to 30% e.g. around 25% of available functional end groups. When the anti-coagulant entities are anionic (for example, in the case of heparin moieties), the number that may be attached will also depend on whether it is desired for the resultant derivatised hyperbranched polymer to have a net positive charge (in which case there should not be too many anionic anti-coagulant entities covalently attached) or a net negative charge.

Coupling of the Anti-Coagulant Entity to the Cationic Hyperbranched Polymer

Typically, each anti-coagulant entity is covalently connected to a cationic hyperbranched polymer via a linker and optionally one or more spacers. The linker is formed by the reaction of a functional end group on the hyperbranched polymer with a functional group on the anti-coagulant entity. Table 3 and Scheme 4 show examples of some types of linkers suitable for attaching the anti-coagulant entity to the hyperbranched polymer along with the functional groups from which the covalent linker is formed and the type of reaction used. See e.g. reference (ISBN: 978-0-12-370501-3, Bioconjugate techniques, $2^{nd}$ ed. 2008). However, radical coupling reactions may also be contemplated.

For each linker, one of the functional end groups is on the hyperbranched polymer and the other is on the anti-coagulant entity. In principle, either way round is possible i.e. by reference to Table 3, functional groups 1 and 2 may respectively be on the hyperbranched polymer and on the anti-coagulant entity or may respectively be on the anti-coagulant entity and on the hyperbranched polymer.

In some cases, the anti-coagulant entity and the hyperbranched polymer may be joined by a linker which comprises more than one functional group. For example, in the case where the linker is a thioether, a bifunctional molecule (having, for example an SH group at each end) can be connected at each end, respectively, to an alkyne/alkene functionalized anti-coagulant entity and an alkyne/alkene functionalized hyperbranched polymer molecule resulting in the linker containing two thioethers. Alternatively, a bis-alkyne/alkene molecule can be connected at each end, respectively, to a thiol functionalized anti-coagulant entity and a thiol functionalized hyperbranched polymer also resulting in the linker containing two thioethers. Similar possibilities exist for other linker types, as is clear from Table 3. The hyperbranched polymer may also carry two or more different functional groups, for example amine and alkyne functionality, so that anti-coagulant entities may be attached to the functional end groups of the hyperbranched polymer via more than one type of linker, however, we prefer attaching anti-coagulant entity using one type of linker.

The linker moiety will typically have a molecular weight of around 14 to 200 e.g. 14 to 100 Da.

TABLE 3

| Type of reaction | Func. group 1 | Func. group 2 | Linker |
|---|---|---|---|
| Reductive amination | *~NH₂ | *~CHO | *~NH~* |
| Amidation | *~NH₂ | *~COOH | *~NH−C(O)~* |
| Michael addition | *~NH₂ | *−C(O)−CH=C(O)−* | *~N(H)−CH(C(O)*)−C(O)* |
| Michael addition | *~SH | *−C(O)−CH=CH−* | *~S−CH(*)−C(O)* |
| Thiol-Ene Click | *~SH | *~CH=CH₂ | *~S~* |
| Thio-Bromo | *~SH | *~Br | *~S~* |

TABLE 3-continued

| Type of reaction | Func. group 1 | Func. group 2 | Linker |
|---|---|---|---|
| Thiol-Yne Click | *∼SH | *≡ | *∼S∼*, *∼S∼* (dithioether) |
| CuAAC Click | *∼N₃ | *≡ | triazole linker |
| Amidation (NHS-activated) | *∼NH₂ | NHS ester | *∼NH-C(O)-* |
| Amidation/ Disulfide (SPDP) | *∼NH₂ | *∼SH | *∼NH-C(O)-CH₂CH₂-S-S-* |

Illustrative chemistries shown in Table 3 and Scheme 4 are discussed below:

—C—NH—C— Linkage

Reductive amination: A reductive amination, also known as reductive alkylation, is a form of amination that involves the conversion of a carbonyl group to an amine linker via an intermediate imine (Schiff's base). The carbonyl group is most commonly a ketone or an aldehyde.

Scheme 4. Reductive amination

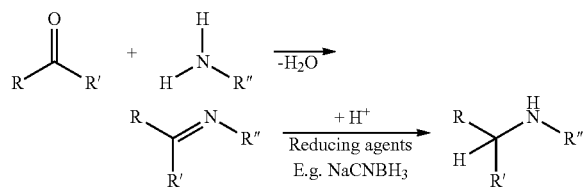

—C—NH—CHR—CHR—C(=O)— Linkage

Michael addition: The Michael reaction or Michael addition is the nucleophilic addition of a carbanion or another nucleophile (e.g. primary amine or thiol) to an alpha, beta unsaturated carbonyl compound. It belongs to the larger class of conjugate additions. This is one of the most useful methods for the mild formation of C—C bonds.

—C—S—C— Linkage

Thio-bromo: Thioether linkages are typically prepared by the alkylation of thiols. Thiols may react with bromide compounds to generate thioether linkages. Such reactions are usually conducted in the presence of base, which converts the thiol into the more nucleophilic thiolate.

Thiol-Ene and Thiol-Yne: Alternatively, thioether linkages may be prepared by reaction of a first compound containing a thiol group with a second compound containing an alkene or an alkyne group. The first and second compounds can each be the hyperbranched polymer molecule and the anti-coagulant entity as appropriate.

Suitably the reaction takes place in the presence of a reducing agent such as tris(2-carboxyethyl)phosphine hydrochloride, or alternatively dithiothreitol or sodium borohydride, to avoid or reverse the effective of undesirable coupling of two thiol groups through oxidation.

In one embodiment the reaction is initiated with a radical initiator. An example of a radical initiator is 4,4'-azobis(4-cyanovaleric acid). Further examples are potassium persulfate, 2,2'-azobis[2-(2-imidazolin-2-yl)propane] dihydrochloride, azobisisobutyronitrile (AIBN), 1,2-bis(2-(4,5-dihydro-1H-imidazol-2-yl)propan-2-yl)diazene dihydrochloride, 2,2'-(diazene-1,2-diyl)bis(2-methyl-1-(pyrrolidin-1-yl)propan-1-imine) dihydrochloride, 3,3'-((diazene-1,2-diylbis(1-imino-2-methylpropane-2,1-diyl))bis(azanediyl))dipropanoic acid tetrahydrate, benzophenone and derivatives of benzophenone such as 4-(trimethyl ammoniummethyl) benzophenone chloride. A further example is ammonium persulfate.

In another embodiment, the reaction is not initiated with a radical initiator. Instead, conditions of higher pH (e.g. pH 8-11) are used. This type of reaction is more suitable when an activated alkene or alkyne is used for reaction with the thiol.

The reaction between a first compound containing a thiol group and a second compound containing an alkyne group may be represented as follows:

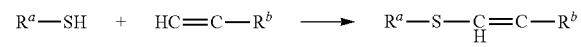

where one of $R^a$ and $R^b$ is the hyperbranched polyamine and the other of $R^a$ and $R^b$ is the anti-coagulant entity.

When an alkene containing linker is formed, this compound may undergo a further chemical transformation with e.g. a thiol (as shown in Table 3) or an amine.

Where the second compound is derivatised with an alkene, in one embodiment an activated alkene is used. An example of a suitable activated alkene is a maleimide derivative.

The reaction between a first compound containing a thiol group and a second compound containing a maleimide group may be represented as follows:

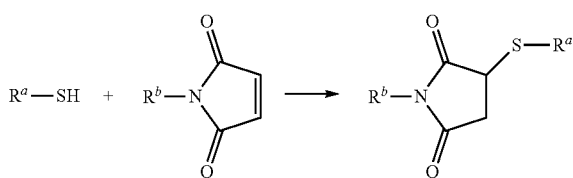

where one of $R^a$ and $R^b$ is the polymer and the other of $R^a$ and $R^b$ is the anti-coagulant entity. The reaction is generally carried out in the presence of tris(2-carboxyethyl)phosphine hydrochloride as reducing agent, and 4,4'-azobis(4-cyanovaleric acid) as radical initiator, and under acidic conditions.

Triazole Linkage (CuAAC Coupling)

Azide-Alkyne: 1,2,3-triazole linkages may be prepared by reaction of an alkyne and an azido compound. The reaction to form the linker may be between an alkyne group on one of the anti-coagulant entity and the hyperbranched polymer molecule and an azido group on the other of the anti-coagulant entity and the hyperbranched polymer molecule. Methods for carrying out this reaction are similar to the methods described in WO 2010/029189.

The reaction between the azide and the alkyne groups may be carried out at elevated temperatures (T>60° C.) or in the presence of a metal catalyst, for example a copper, e.g. a Cu(I) catalyst using reaction conditions conventionally used in the Huisgen cycloaddition (the 1,3-dipolar cycloaddition of an azide and a terminal alkyne to form a 1,2,3-triazole). The Cu(I) catalyst may, if desired, be produced in situ, e.g. by reduction of a corresponding Cu(II) compound for example using sodium ascorbate. The reaction may also, if desired, be carried out under flow conditions.

The CuAAC reaction may, for example be carried out at a temperature of from about 5 to 80° C., preferably at about room temperature. The pH used in the reaction may be from about 2-12, preferably about 4-9 and most preferably at about 7. Suitable solvents include those in which the entity attached to the azide or alkyne is soluble, e.g dimethylsulfoxide, dimethylformamide, tetrahydrofuran and preferably water or mixtures of water with one of the above. The proportion of the entity to the surface may be adjusted to provide the desired density of the entity on the surface.

—C(=O)—N— Linkage

Amidation: Amides are commonly formed via reactions of a carboxylic acid with an amine. Carboxylic acids and carboxylic acid derivatives may undergo many chemical transformations, usually through an attack on the carbonyl breaking the carbonyl double bond and forming a tetrahedral intermediate. Thiols, alcohols and amines are all known to serve as nucleophiles. Amides are less reactive under physiological conditions than esters.

Amidation using activated acid: Activated acids (basically esters with a good leaving group e.g. NHS-activated acids) can react with amines to form amide linkers, under conditions where a normal carboxylic acid would just form a salt.

—C—S—S—CH$_2$—CH$_2$—C(=O)—N— Linkage

Coupling using SPDP reagents: The N-succinimidyl 3-(2-pyridyldithio) propionate (SPDP) and its analogues belong to a unique group of amine- and thiol-reactive heterobifunctional link forming reagents that produce disulfide-containing linkages.

Reductive amination, Michael addition, thio-bromo reactions, amidation using NHS-activated acid, coupling using SPDP reagent, CuAAC and thiol-ene couplings are all suitable to provide benign coupling conditions and high yield of linker formation.

The groupings shown in Table 3 are for illustrative purposes only and alternative or variant functionalities may of course be employed. For example, the amine groups may be positioned on a secondary carbon or the aliphatic chains illustrated may be replaced by aromatic groups.

Free Radical Initiated Reactions

As mentioned briefly above, the functional end groups of the hyperbranched polymer molecule may be coupled to an anti-coagulant entity by a linker formed through a free radical initiated reaction. Radicals may be created for example via heat, photolysis (e.g. Norrish type I and/or Norrish type II reactions), ionization, oxidation, plasma or electrochemical reactions For example when a hyperbranched polymer molecule that has free primary amine groups is treated with benzophenone, radicals such a e.g. carbon or oxygen radicals are created which may participate in free radical initiated reactions (such as reaction with alkenes).

In one embodiment the covalent linker comprises a secondary amine linkage. In particular, the linker may comprise a —NH— group;

In another embodiment, the covalent linker comprises an amide linkage. In particular, the linker may comprise a —NH—C(O)— group;

In another embodiment the covalent linker comprises a thioether linkage.

In another embodiment, the covalent linker comprises a 1,2,3-triazole linkage.

The term "thioether linkage" refers to a connection between a sulfur and two carbon atoms. This connection is sometimes referred to as "sulfide". The sulfur may be attached to two saturated carbon atoms (i.e. —C—S—C—) or it may be attached to a saturated and an unsaturated carbon atom (i.e. —C—S—C=).

The term "thiol" refers to an —S—H moiety.

The term "secondary amine linkage" refers to a connection between an NH group and two carbon atoms, i.e. —C—NH—C—.

The term "amide linkage" refers to a connection between two carbon atoms of the type —C—C(O)NH—C—.

In one embodiment, the linker between the anti-coagulant entity such as a heparin moiety and a functional end group of the hyperbranched polymer molecule is an unbranched linker.

The linker can be biodegradable or non-biodegradable but is more suitably non-biodegradable in order that a coated device is non-thrombogenic for a long period of time.

Where there is a multiplicity of linkers it is possible for some or all of them to be of a different type.

In one embodiment, all of the linkers are of the same type.

Spacers

At its simplest the covalent connection between the functional end group of the hyperbranched polymer molecule and the anti-coagulant entity is via a linker e.g. as shown in Table 3. However optionally the linker may be separated by a spacer from either the surface or the anti-coagulant moiety or both.

The purpose of the spacer, if employed, is usually to significantly increase the separation between the hyperbranched polymer molecule and the anti-coagulant entity i.e. in effect to significantly increase the separation between the surface of the device and the anti-coagulant entity. For example, the molecular weight of the spacer may be from 50 to $10^6$ Da, typically 100 to $10^6$ Da e.g. 100 to $10^4$ Da. The length of the spacer may for example be from 10 to $10^3$ Å. We prefer the spacer to be straight chain. In some embodiments the spacer is hydrophilic, for example, it may comprise a PEG chain. In one aspect, the covalent connection between the functional end group of the hyperbranched polymer molecule and the anti-coagulant entity may be viewed as having three portions—"spacer A" between the functional end group of the hyperbranched polymer molecule and the linker moiety, the linker moiety, and "spacer B" between the linker moiety and the entity. In one embodiment the molecular weight of spacer A is between 50 and $10^3$ Da. In another embodiment the molecular weight of spacer B is between 50 and $10^3$ Da. In one embodiment spacer A comprises one or more aromatic rings. In another embodiment spacer A does not comprise any aromatic rings. In one embodiment spacer B comprises one or more aromatic rings. In another embodiment spacer B does not comprise any aromatic rings. In one embodiment spacer A is hydrophilic. In another embodiment spacer B is hydrophilic. In one embodiment spacer A comprises a PEG chain. In another embodiment spacer B comprises a PEG chain. In one embodiment spacers A and B are both hydrophilic, for example they each comprise a PEG chain. As used herein, a PEG chain refers to a polymeric chain obtainable by polymerisation of ethylene oxide, typically of weight between 100 and $10^6$ Da. In another aspect, the covalent connection may comprise two or more triazole rings. In another embodiment, the covalent connection may be viewed as having five portions—"spacer A" between the surface and a first linker moiety, the first linker moiety, "spacer B" between the first linker moiety and a second linker moiety, the second linker moiety, and "spacer C" between the second linker moiety and the entity. In one embodiment the molecular weight of spacer A is between 50 and $10^3$ Da. In one embodiment the molecular weight of spacer B is between 100 and $10^6$ Da. In one embodiment the molecular weight of spacer C is between 50 and $10^3$ Da. In one embodiment spacer A and/or spacer B and/or spacer C is hydrophilic for example comprising a PEG chain. For example spacer B (at least) may comprise a PEG chain.

Although spacers may be present they are typically not necessary since it should be noted that the structure of the hyperbranched polymers, by virtue of their size and shape, provides for some separation of the anti-coagulant entity from the surface of the device.

In cases where spacers are present, they are for example straight chain spacers of about 10 to $10^3$ Å.

A specific merit of having a spacer that comprises a PEG chain (or other hydrophilic polymer) is to provide the device with lubricious properties.

The spacer can be biodegradable or non-biodegradable but is more suitably non-biodegradable in order that a coated device is non-thrombogenic for a long period of time (i.e. the coated device has preserved non-thromogenic properties).

Functionalization of Coating Building Blocks i. Linker formation where no prior modification of hyperbranched polymer molecule or anti-coagulant entity is required Several of the linkers shown above in Table 3 can be formed directly by the reaction of a functional end group of a hyperbranched polymer, for example a hyperbranched polyamine with an anti-coagulant entity containing an aldehyde.

Thus, the reductive amination, the Michael addition, the SPDP reaction and the amidation reactions shown in Table 3 require the presence of a primary amine functional end group.

Hyperbranched molecules such as hyperbranched polyamines e.g. PAMAM dendrimers possess suitable free primary amine groups for use in these linkage forming reactions and therefore do not require further modification.

Therefore, in one embodiment, the hyperbranched polymer molecule carries multiple free primary amine groups as functional end groups and is, for example, a PAMAM, PPI or PEI hyperbranched polymer molecule.

Nitrous acid degraded heparin and native heparin bear reactive groups, an aldehyde group and a hemi-acetal function respectively, at their reducing end and thus nitrous acid degraded heparin or native heparin can be reacted with a hyperbranched polymer having free primary amine groups in a reductive amination reaction to form a linker containing a secondary amine group as shown in Table 3 and Scheme 4 above.

Methods of forming a secondary amine linkage between an amine functionalized surface and a heparin derivative are described, for example in EP-B-0086186, EP-B-0086187, EP-B-0495820 and U.S. Pat. No. 6,461,665.

ii. Linkage formation where modification of hyperbranched polymer and/or anti-coagulant entity is required Alternatively, either or both of the anti-coagulant entity and the hyperbranched polymer may be modified to carry a suitable functional group as will be discussed in greater detail below.

Methods of derivatising heparin and other anti-coagulant entities e.g. to incorporate alkyne and azide groups are disclosed in WO2010/029189 the contents of which are herein incorporated by reference in their entirety.

Therefore, for some of the linkers described above in Table 3, it is necessary to pre-prepare functionalized derivatives of either or both of the hyperbranched polymer molecule and the anti-coagulant entity.

The hyperbranched polymer molecule may be functionalized using techniques known in the art. Primary amino groups on a PAMAM dendrimer or similar hyperbranched polymer may be used as points of attachment for a suitable functional group for forming the chosen covalent linkage, for example an alkene, alkyne, thiol, halo or azido group. Hence hyperbranched polyamines may be functionalized to bear alkene, alkyne, thiol, halo or azido groups by conventional means e.g. by reacting pendant primary amino groups on the polyamine with an activated carboxylic acid (e.g. an N-hydroxy succinimide derivative of a carboxylic acid) containing an alkene, alkyne, thiol, halo or azido group.

Thus, in order to introduce suitable alkene or alkyne groups, a hyperbranched polyamine molecule bearing a number of primary amine groups represented as follows:

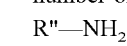

where R" is the hyperbranched polyamine residue; may be reacted with a compound of the formula:

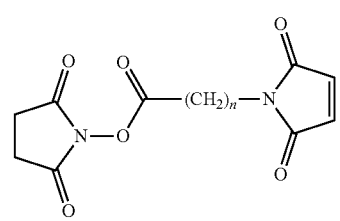

where n is an integer from 1 to 8 e.g. 1 to 4;

to give a maleimide functionalized polyamine of the formula:

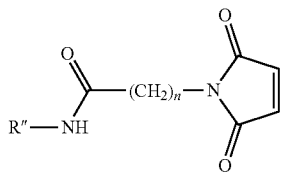

where R" and n are as defined above.

Alternatively, the hyperbranched polyamine may be reacted with an activated alkyne-containing group of the formula:

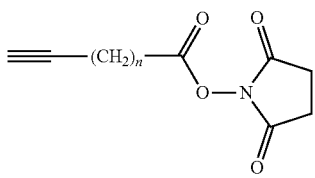

where n is an integer from 1 to 8 e.g. 1 to 4;
to give an alkyne functionalized hyperbranched polyamine of the formula:

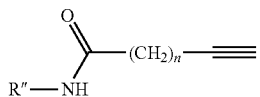

where R" and n are as defined above.

Similarly, a hyperbranched polymer having free primary amines as functional end groups may be derivatised with a thiol group. In this case, a hyperbranched polyamine such as a PAMAM dendrimer bearing a number of primary amine groups represented as follows:
R"—NH$_2$
where R" is as defined above;
may be reacted with an thiol-containing activated carboxylic acid, for example a compound of the formula:

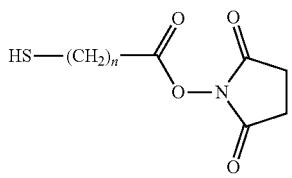

where n is an integer from 1 to 8 e.g. 1 to 4;
to give a derivatised polymer of the formula:

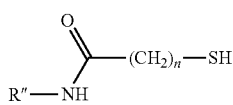

where R" and n are as defined above.

Halo groups may be introduced into the hyperbranched polymer molecule in a similar manner.

One may also consider using other amidation reactions involving SPDP or 1-Ethyl-3-(3-dimethylaminopropyl)-carbodiimide (EDC) to obtain the same functionalization.

An anti-coagulant entity, e.g. heparin, carrying an alkene, aldehyde, alkyne, thiol, azo, amine, halide, activated carboxylic acid, maleimide ester or an α,β-unsaturated carbonyl group may be made by conventional methods known per se. For example an anti-coagulant entity, e.g. heparin, carrying an alkyne/alkene group may be made by the reaction of an alkoxyamine of the formula:

$$R^1\text{—}O\text{—}NH_2$$

wherein $R^1$ is an alkyne/alkene-containing group; with an aldehyde or hemi-acetal group on the anti-coagulant entity using conventional techniques known per se, see e.g. Example 3a, 3b and 3c of WO2010/029189. This type of reaction proceeds via formation of an oxy-imine function to give a compound of the formula:

$$R^1\text{—}O\text{—}N\text{=}R'$$

in which $R^1$ is as defined above and R' is the residue of the anti-coagulant entity.

Nitrous acid degraded heparin and native heparin bear reactive groups, an aldehyde group and a hemi-acetal function respectively, at their reducing end which may be linked in this way.

Similarly, an anti-coagulant entity derivatised with a thiol group may be formed by the reaction of an aldehyde or hemi-acetal group on the anti-coagulant entity with a compound of the formula:

$$HS\text{—}X\text{—}NH_2$$

where X is a hydrocarbon spacer, for example $(CH_2)_n$ where n is 1 to 8 e.g. 1 to 4, in which one or more (e.g. 1 or 2) methylene groups are optionally replaced by 0; or X comprises a PEG chain containing 1 to 100 (e.g. 1 to 50 such as 1 to 10) ethylene glycol units;
to give a product of the formula $$R'\text{—}CH_2\text{—}NH\text{—}X\text{—}SH$$

where X is as defined above and R'—CH$_2$— is the residue of the anti-coagulant entity.

An example of such a procedure is given in Example 4.2 below.

A similar method can be employed for the introduction of an azido group or a halo group such as fluoro, chloro or bromo.

As discussed above, one reason to modify the hyperbranched polymer is to introduce certain functional groups to permit coupling to the anti-coagulant entity. When the hyperbranched polymer has certain existing functional end groups e.g. primary amine groups, these may be converted to other functional groups, for example, azide or alkyne groups. All or (more usually) some (e.g. 0.5 to 25%) of the functional groups may be converted for this purpose.

It may also be desired to introduce new functional groups for other purposes. For example some (e.g. 0.5 to 25%) existing functional end groups (e.g. primary amine groups) may be converted to other functional groups, for example, azide or alkyne groups to permit attachment of beneficial agents e.g. lubricious agents mentioned below.

Surface Coating

The device has a surface comprising a layered coating formed of one or more layers. The device, especially when it is a medical device, may have one or more portions containing void spaces, or pores. The pores may be within the device and/or be part of at least one surface of the device.

An example of a porous medical device is expanded polytetrafluoroethylene (ePTFE). The pores may have a coating layer or not.

Desirably a portion of the surface (desired to be non-thrombogenic) or the whole of the surface of the device is covered with a coating.

The surface of a device may have one or many coating layers (e.g. 2 or more, or 3 or 4 or 5 e.g. up to 20 coating layers) and the term "outer coating layer" refers to a coating layer which, in a medical device, is in contact with the tissues of the patient or is in contact with body fluids, or in an analytical or separation device, comes into contact with a substance to be analysed, separated or handled. Thus, the outer coating layer may be the coating layer on the outer and/or the inner surface of a hollow device or a device of open structure such as a stent. A layer which is not the outer coating layer is referred to herein as an "underlayer".

According to the invention the outer coating layer comprises a plurality of cationic hyperbranched polymer molecules to which are covalently attached via functional end groups one or more anti-coagulant entities.

In general, the majority, or even all, of the cationic hyperbranched polymer molecules of the outer coating layer will have a plurality of anti-coagulant entities covalently attached thereto via their functional end groups.

The optimum number of layers will depend on the type of material from which the device is made, and the contemplated use of the surface coating. The number and nature of the layers needed to provide a full coverage of the device surface can be easily determined by those skilled in the art. The surface coating may, if desired, be made up layer by layer.

For example, the coating layer(s) may be formed by adsorbing on the surface of the device a cationic polymer, followed by the application of a solution of an anionic polymer, e.g. an anionic polysaccharide, e.g. dextran sulfate or a functionalized cationic hyperbranched polymer with a net negative charge, to obtain at least one adsorbed layer of the anionic polymer. See Multilayer Thin Films ISBN: 978-3-527-30440-0. Hence the surface may comprise a layer of cationic polymer and a layer of anionic polymer e.g. a polysaccharide or a functionalized cationic hyperbranched polymer with a net negative charge. More generally, the surface coating may comprise one or more coating bilayers of cationic polymer and anionic polymer. Typically the innermost layer (i.e. the layer applied to the bare device surface, for example a metal, plastic or ceramic surface) is a layer of cationic polymer.

As discussed in more detail below, the outer coating layer comprising a plurality of cationic hyperbranched polymer molecules to which are covalently attached one or more anti-coagulant entities via their functional end groups may be applied in one of two ways. According to the first way, cationic hyperbranched polymer molecules with a general positive charge may be applied to an anionic polymer on the surface of the device. The hyperbranched polymer molecules are then modified to link them to the anti-coagulant entities. According to the second way, cationic hyperbranched polymer molecules to which are covalently attached one or more anti-coagulant entities via their functional end groups may be applied to an anionic or cationic polymer on the surface of the device depending on whether the functionalised hyperbranched polymer molecules bear an overall positive or negative charge.

In some cases, the cationic hyperbranched polymer molecules may be cross-linked to the polymer surface coating via reactive functional groups. If the cationic hyperbranched polymer is cross-linked to the device surface or to underlying coating layers before reaction with the anti-coagulant entity, it is necessary to ensure that a sufficient number of amino groups (or other reactive groups introduced) remain available to be able to link the desired amount of anti-coagulant entity to the outer coating layer. Alternatively, the cationic hyperbranched polymer molecules can be reacted with the anti-coagulant entities before application to the surface of the device or to a coating layer and then cross-linked. Typically there is no cross-linking directly between the anti-coagulant entity and the surface coating.

A range of cationic polymers may be used for the underlayers. An exemplary cationic polymer is a polyamine (e.g. that described in EP 0086187 Larsson and Gölander). Such polymers may be a straight chain but is more usually a branched chain polymer or alternatively a hyperbranched polymer, optionally cross-linked. Alternatively, one or more (e.g. all of) the cationic polymer layers other than the outer coating layer may comprise (e.g. be formed of) cationic hyperbranched polymer molecules, which are the same as or similar to those used in the outer coating layer. Optionally these may also be cross-linked.

The coating procedure may be performed essentially as described in EP-B-0495820 and in this case it is only the outer coating layer which comprises the anti-coagulant entity.

The procedure of EP-B-0495820 may however be modified so that the outer layer is the anionic polymer which is then coupled, as described below, with a cationic hyperbranched polymer to which is attached one or more anti-coagulant entities (but that still retains a net positive charge) or is coupled with a cationic hyperbranched polymer with functional end group(s) capable of reacting with functional groups on an anti-coagulant entity to form a covalent linker moiety as described above.

According to one embodiment, there is provided a device wherein one or more of the layers of the layered coating other than the outer coating layer comprises cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups which are optionally derivatised e.g. with one or more anti-coagulant entities.

According to one embodiment of the invention when underlayers comprise cationic polymers they may comprise cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups. According to this embodiment, these cationic hyperbranched polymer molecules may be the same as those used in the outer coating layer (but without the anti-coagulant entity attached) or they may be different hyperbranched polymer molecules. In any event exemplary cationic hyperbranched polymer molecules include those described elsewhere herein in relation to those cationic hyperbranched polymer molecules that may be used in preparation of the outer coating layer.

For example, all the underlayers which comprise cationic polymers may comprise cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1); and (iv) functional end groups.

The anionic polymer may also be a functionalized cationic hyperbranched polymer with a net negative charge.

According to one embodiment, when underlayers comprise anionic polymers they may comprise cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anionic anti-coagulant entity covalently attached thereto thereby conferring on the molecules a net negative charge.

For example, all the underlayers which comprise anionic polymers may comprise cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anionic anti-coagulant entity covalently attached thereto thereby conferring on the molecules a net negative charge.

According to one embodiment, the layers of the coating on the surface of the device are all either (a) cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups or (b) cationic hyperbranched polymer molecules characterized by having (i) a core moiety of molecular weight 14-1,000 Da (ii) a total molecular weight of 1,500 to 1,000,000 Da and (iii) a ratio of total molecular weight to core moiety molecular weight of at least 80:1 (e.g. at least 100:1) and (iv) functional end groups, whereby one or more of said functional end groups have an anionic anti-coagulant entity covalently attached thereto thereby conferring on the molecules a net negative charge.

One advantage of this is that the number of different components of the layers of the coating is minimized.

Prior to applying the first coating layer (i.e. the innermost layer), the surface of the device may be cleaned to improve adhesion and surface coverage. Suitable cleaning agents include solvents as ethanol or isopropanol (IPA), solutions with high pH like solutions comprising a mixture of an alcohol and an aqueous solution of a hydroxide compound (e.g. sodium hydroxide), sodium hydroxide solution as such, solutions containing tetramethyl ammonium hydroxide (TMAH), basic Piranha (ammonia and hydrogen peroxide), acidic Piranha (a mixture of sulfuric acid and hydrogen peroxide), and other oxidizing agents including combinations of sulfuric acid and potassium permanganate or different types of peroxysulfuric acid or peroxydisulfuric acid solutions (also as ammonium, sodium, and potassium salts).

Thus an aspect of the invention is a device having a surface coating wherein the surface coating comprises one or more coating bilayers of cationic polymer and anionic polymer, wherein the outer coating layer of the coating comprises a plurality of cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anti-coagulant entity covalently attached thereto.

Formation of the Outer Coating Layer

Figure 7:
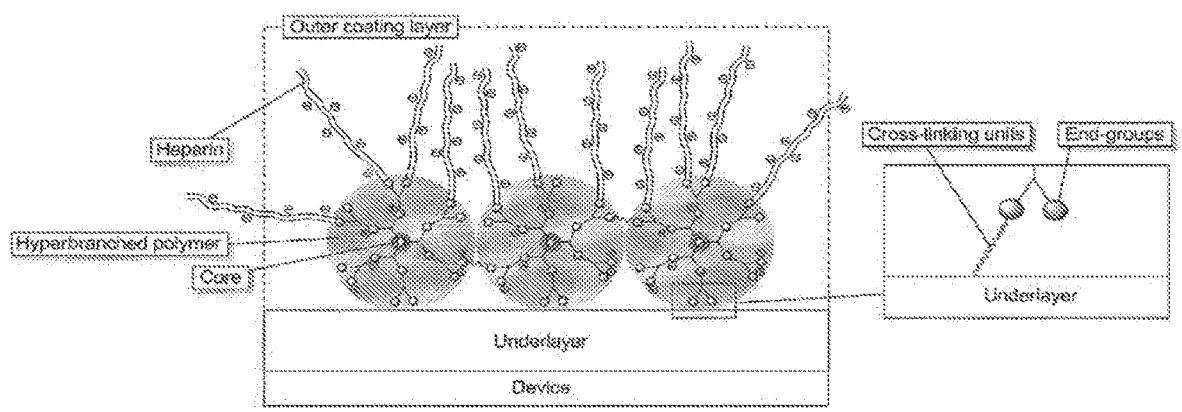
FIG. 7 is a schematic representation of the components of the invention. It shows how the hyperbranched polymers, bearing anti-coagulant entities, in the outer coating layer interact (involving covalent bonds and/or ionic interactions) with the underlayer and other hyperbranched polymers in the outer coating layer.

As briefly described above, the heparin moiety or other anti-coagulant entity may be attached to the hyperbranched polymer molecules either before or after the hyperbranched polymer molecules are applied to the surface of the device. The surface of the device to which the outer coating layer is applied may optionally contain one or more underlayers. See FIG. 7.

Therefore, in a further aspect of the invention there is provided a process for the manufacture of a device as described above, the process comprising, in any order:
 i. reacting a plurality of functional end groups of hyperbranched polymer molecules with anti-coagulant entities such that each hyperbranched polymer molecule is covalently linked to a plurality of anti-coagulant entities; and
 ii. attaching the hyperbranched polymer molecules to the surface of a device.

As described above, the anti-coagulant entities are attached to hyperbranched polymer molecule via a covalent linkage and it may, in some cases, be necessary to carry out an additional step of modifying the hyperbranched polymer molecules and/or the anti-coagulant entity before step (i) in order to introduce suitable functional groups for forming a covalent linkage between the hyperbranched polymer molecules and the anti-coagulant entity.

Suitable covalent linkages and methods for modifying the hyperbranched polymer and/or the anti-coagulant entity are discussed in detail above. As noted above, the linker may optionally be separated from the surface and/or the anti-coagulant moiety by a spacer. Thus the process may optionally involve the modification of the surface and/or the anti-coagulant moiety by provision of a spacer.

When the first step of the process above is step (i), the process of attaching the anti-coagulant entities to the hyperbranched polymer molecules may be carried out in solution under appropriate reaction conditions with suitable solvents being, for example THF, DCM, DMF, DMSO, IPA, methanol, ethanol and water including mixtures thereof.

When the second step of the process is step (i) (i.e. the first step of the process is step (ii)), the outer coating layer of the device will usually be brought into contact with a solution of the anti-coagulant entity under the appropriate reaction conditions. Suitable solvents for the anti-coagulant entity are, for example, IPA, ethanol, THF, DMF, DMSO, DCM and especially water including mixtures thereof.

In one embodiment, as already mentioned, two or more hyperbranched polymer molecules may be aggregated by cross-linking.

Therefore, the process above may further comprise the additional step of cross-linking two or more hyperbranched polymer molecules to one another. The two or more hyperbranched polymer molecules may be aggregated by cross-linking before or after the hyperbranched polymer molecules are functionalized with the one or more anti-coagulant entities. The order in which cross-linking is performed may depend on the device e.g. the geometry of the device. Preferably the cross-linking is performed after the functionalisation. Furthermore, this cross-linking step may take place either before or after the attachment of the hyperbranched polymer molecules to the surface of the device.

The process may also include the step of cross-linking one or more hyperbranched polymer molecules to the surface of the device. For example hyperbranched polymer molecules to which are attached one or more anti-coagulant entities on the outer coating layer may also be cross linked to a cationic or anionic polymer of the layer underneath the other coating layer.

This cross-linking step may be part of step (ii) above or, alternatively the cross-linking step may be carried out after step (ii) in order to strengthen the adhesion of the hyperbranched polymer molecules to the surface of the device and enhance the stability of the coating.

If any required cross-linking, either between two or more hyperbranched polymer molecules or between hyperbranched polymer molecules and the surface, is carried out before derivatisation, it is necessary to ensure that sufficient free functional groups remain on the hyperbranched molecule to allow attachment of a suitable number of anti-coagulant entities. Alternatively, if derivatisation is carried out first, then the degree of derivatisation must be such that free functional groups remain for any cross-linking that is required.

In general, it is preferred that step (i) is carried out before step (ii) since it is easier to control the amount of anti-coagulant entity which is attached to the hyperbranched polymer molecules and, in addition, wastage of anti-coagulant entity is minimized, particularly when the reaction is carried out in solution as described above.

We provide as an aspect of the invention a device obtainable by the aforementioned processes.

Another aspect of the invention is a non-thrombogenic device which is obtainable by a process comprising:
   (a) treating a device to present a surface coating comprising an outer coating layer comprising cationic hyperbranched polymer molecules characterized by having (i) a core moiety of molecular weight 14-1,000 Da (ii) a total molecular weight of 1,500 to 1,000,000 Da and bearing functional end groups and (iii) a ratio of total molecular weight to core moiety molecular weight of at least 80:1 (e.g. at least 100:1);
   (b) reacting one or more of said functional end groups with molecules of an anti-coagulant entity which is functionalized to bear groups which are capable of reacting with the reactive functional groups on the hyperbranched cationic polymer;
   thereby to attach the anti-coagulant entity to the hyperbranched cationic polymer.

Another aspect of the invention is a non-thrombogenic device which is obtainable by a process comprising:
   (a) treating a device to present a positively charged polymer surface layer;
   (b) associating with said polymer surface layer functionalized cationic hyperbranched polymer molecules characterized by having (i) a core moiety of molecular weight 14-1,000 Da (ii) a total molecular weight of 1,500 to 1,000,000 Da and (iii) a ratio of total molecular weight to core moiety molecular weight of at least 80:1 (e.g. at least 100:1) and bearing a multiplicity (e.g. 2 or 10 or 50 or 100 or 500 or more depending on the number of available functional end groups) of negatively charged anti-coagulant entities such as heparin moieties and wherein said functionalized hyperbranched polymer has a net negative charge.

Another aspect of the invention is a non-thrombogenic device which is obtainable by a process comprising:
   (a) treating a device to present a negatively charged polymer surface layer;
   (b) associating with said polymer surface layer functionalized cationic hyperbranched polymer molecules characterized by having (i) a core moiety of molecular weight 14-1,000 Da (ii) a total molecular weight of 1,500 to 1,000,000 Da and (iii) a ratio of total molecular weight to core moiety molecular weight of at least 80:1 (e.g. at least 100:1) and bearing one or more negatively charged anti-coagulant entities such as heparin moieties and wherein said functionalized hyperbranched polymer has a net positive charge.

For example, the device is treated to present a surface comprising an anionic polymer for example a polysaccharide such as dextran sulfate, derivatives thereof or a functionalized cationic hyperbranched polymer with a net negative charge.

Cross Linking

As described herein, hyperbranched polymer molecules of the outer coating layer may optionally be cross-linked to other hyperbranched polymer molecules of the outer coating layer or may be cross-linked to molecules (e.g. hyperbranched polymer molecules) of an underlayer. Polymer molecules in underlayers may optionally be cross linked.

Suitably cross linking agents that may be used for these purposes will be chosen according to the coupling chemistry required. Any di, tri, or multi functional cross-linker may, in principle, be used such as functionalised PEGs and Jeffamines. For cross linking of amines it would be suitable to use di-functional aldehydes such as crotonaldehyde or glutaraldehyde. In some cases epichlorohydrin may be useful.

Cross linking is capable of creating a covalent bond between a functional end group of the hyperbranched polymer molecule of the outer coating layer and a functional end group of another hyperbranched polymer molecule of the outer coating layer or a molecule (e.g. a hyperbranched polymer molecule or a cationic or anionic polymer molecule) of an underlayer. Such cross-linking suitably does not involve the anti-coagulant entity. Thus suitably the anti-coagulant entity has a covalent connection only to one hyperbranched polymer molecule and not to any other molecule. Suitably the cross linking of one hyperbranched polymer molecule to another hyperbranched polymer molecule involves use of functional end groups on the hyperbranched polymer molecule which are not involved in linkage to the anti-coagulant entity. In one embodiment said functional groups used in cross-linking are formed by refunctionalisation of the original functional end groups of the hyperbranched polymer molecule.

Devices

The device may be any device to which it is desirable to attach anti-coagulant entities, for example a medical device, an analytical device or a separation device.

For the purposes of this patent application, the term "medical device" refers to implantable or non-implantable devices but more usually to implantable medical devices. Examples of implantable medical devices which may be permanent or temporary implantable medical devices include catheters, stents including bifurcated stents, balloon expandable stents, self-expanding stents, stent-grafts including bifurcated stent-grafts, grafts including vascular grafts, bifurcated grafts, artificial blood vessels, blood indwelling monitoring devices, artificial heart valves, pacemaker electrodes, guidewires, cardiac leads, cardiopulmonary bypass circuits, cannulae, plugs, drug delivery devices, balloons, tissue patch devices and blood pumps. Examples of non-implantable medical devices are extracorporeal devices, e.g. extracorporeal blood treatment devices, and transfusion devices.

Devices may have neurological, peripheral, cardiac, orthopedal, dermal and gynecological application, inter alia.

A medical device may have one or many coating layers and the term "outer coating layer" refers to a coating layer which, when the device is implanted in a patient or is in use, is in contact with the tissues of the patient or is in contact with body fluids e.g blood. Thus, the outer coating layer may be the coating layer on the outer and/or the inner surface of a hollow device or a device of open structure such as a stent.

An analytical device may be, for example, a solid support for carrying out an analytical process such as chromatography or an immunological assay, reactive chemistry or catalysis. Examples of such devices include slides, beads, well plates, membranes etc. A separation device may be, for example, a solid support for carrying out a separation process such as protein purification, affinity chromatography or ion exchange. Examples of such devices include filters and columns etc. Like a medical device, an analytical or separation device may also have many coating layers and the term "outer coating layer" refers to a coating layer which comes into contact with a substance to be analysed, separated or handled.

In some cases, it may be desirable to adjust the properties of the coating and in this case one or more additional entities may be attached to the hyperbranched polymer in addition to the anti-coagulant entity. For example, if it is desirable to increase the hydrophilicity of the hyperbranched polymer, the additional entities may comprise one or more PEG chains.

As used herein, the term "PEG chain" refers to a polymeric chain obtainable by polymerisation of ethylene oxide, typically of weight between $10^2$ and $10^6$ Da.

The coating of the device may comprise alternate layers of a cationic polymer and an anionic polymer. The cationic polymer may be a straight chain polymer but is more usually a branched chain polymer, a hyperbranched polymer or a polymer comprising a plurality of (cationic) hyperbranched polymer molecules, wherein, in the outer coating layer, there are covalently attached to said hyperbranched polymer molecules one or more anti-coagulant entities via their functional end groups.

Thus, in one embodiment of the invention, one or more layers of the coating, other than the outer layer, may be formed from the same or similar hyperbranched polymer molecules as the outer layer. Features of such sub-layers may be as described for the outer layer, see Example 2.2 and 3.3.

The device may comprise or be formed of a metal or a synthetic or naturally occurring organic or inorganic polymer or a ceramic material, inter alia.

Thus, for example, it may be formed from a synthetic or naturally occurring organic or inorganic polymer or material such as polyethylene, polypropylene, polyacrylate, polycarbonate, polysaccharide, polyamide, polyurethane (PU), polyvinylchloride (PVC), polyetheretherketone (PEEK), cellulose, silicone or rubber (polyisoprene), plastics materials, metals, glass, ceramics and other known medical materials or a combination of such materials. Other suitable substrate materials include fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), and combinations of the above with and without crosslinking between the polymer chains.

Suitable metals include nickel titanium alloy (Nitinol), stainless steel, titanium, cobalt chromium, gold and platinum. Nitinol and stainless steel are preferred. Titanium is also preferred.

More generally, suitable metals include metallic materials and alloys such as cobalt chromium alloy (ELGILOY), stainless steel (316L), high nitrogen stainless steel, cobalt chrome alloy L-605, MP35N, MP20N, tantalum, nickel-titanium alloy, nitinol, platinum-iridium alloy, gold, magnesium, and combinations thereof.

We prefer the coated surface to which the anti-coagulant entity (e.g. heparin or other heparin moiety) is attached to be such that it retains non-thrombogenic properties after sterilization, e.g. ethylene oxide (EO) sterilization.

Sterilization may be carried out by means well known to those skilled in the art. The preferred method of sterilization is using ethylene oxide gas. Alternatively, other methods such as radiation, e.g. e-beam or gamma radiation, may be used where such radiation will not degrade the object or the coating or both.

A preferred embodiment of the present invention relates to a coated medical device for implantation e.g. permanent implantation, or other placement, at an anatomical site. Other preferred embodiments include temporary use devices such as catheters and extracorporeal circuits. Examples are sterile (e.g. sterilized) medical devices for placement inside an anatomical structure delimiting a void space, or lumen, to reinforce the anatomical structure or maintain the void space. Suitably the attached anti-coagulant entity, e.g. heparin or other heparin moiety, does not elute to any substantial extent and remains with the device. For example, after 15 hour rinse with NaCl (0.15 M) prior to testing the retained AT binding capacity remains adequate (e.g. greater than 1 or 2 or 4 or 5 or 10 pmol/cm$^2$) and/or when tested in the Blood loop evaluation test (see Example 6) with fresh blood from a healthy donor the reduction in platelet count of the blood after the test is substantially lower for the blood exposed to the coated surface according to the invention than that of an uncoated control (e.g. the reduction in platelet count after the test for the blood exposed to the coated surface is less than 20%, preferably less than 15% and more preferably less than 10%).

The non-thrombogenic character of devices according to the present invention may be tested by a number of methods. For example non-thrombogenic character may be associated with having a high antithrombin binding capacity, especially as compared with devices having untreated surfaces.

For example, we prefer the surface of the device e.g. the medical device to have an antithrombin (AT) binding capacity of at least 1 (e.g. at least 5) picomoles AT per square centimeter (pmol/cm$^2$) of surface. In other embodiments, the AT binding capacity is at least 6 pmol/cm$^2$, at least 7 pmol/cm$^2$, at least 8 pmol/cm$^2$, at least 9 pmol/cm$^2$, or at least 10 pmol/cm$^2$ of surface. In some embodiments, the AT binding capacity is at least 100 pmol/cm$^2$ of surface. AT binding capacity can be measured by methods known in the art, e.g. those described in Pasche., et al., in "Binding of antithrombin to immobilized heparin under varying flow conditions" Artif. Organs 15:481-491 (1991) and US 2007/0264308. By way of comparison it may be concluded from Sanchez et al (1997) J. Biomed. Mater. Res. 37(1) 37-42, see FIG. 1, that AT binding values of around 2.7-4.8 pmol/cm$^2$ (depending on the experimental set up) or more do not appear to give rise to significant thrombogenic enzymatic activity upon contact with plasma.

Alternatively or additionally we prefer the surface to be non-thrombogenic due to high capacity to suppress coagulation and other defence systems as shown in the Blood loop evaluation test described in Example 6. According to that test, the surface to be investigated is applied to a PVC tubing which is rinsed for 15 hours with 0.15 M NaCl prior to testing with fresh blood.

The thrombogenicity of an uncoated control surface is indicated by a reduction in platelet count of the exposed blood, measured after the test. The non-thrombogenicity of a surface prepared according to the method described herein is indicated by a reduction in the platelet count of the blood to a substantially lower degree (e.g. the reduction in platelet count after the test for the blood exposed to the coated surface is less than 20%, preferably less than 15% and more preferably less than 10%).

Other similar blood evaluation methods different from the Blood loop model can be performed by those skilled in the art in order to assess thrombogenicity/non-thrombogenicity.

The amount of the anti-coagulant entity bound to a particular surface area can easily be controlled and adjusted by choosing particular sizes and amounts of hyperbranched molecule for the coating.

The distribution of the anti-coagulant entity on the surface can be determined by conventional staining techniques which are known per se, e.g. the distribution of heparin can be determined using toluidine blue.

Beneficial Agents within the Coating

The layered coating of the device, particularly a medical device, may comprise one or more beneficial agents besides the anti-coagulant entities. Exemplary beneficial agents include drug molecules and lubricious agents. The beneficial agent may be introduced to the underlayers or to the outer coating layer.

Beneficial agents may be attached to the coating by a covalent linkage, which may be degradable to allow migration (i.e. elution) of the beneficial agent from the polymer surface or it may not be degradable if long lasting action is required. Alternatively, they may be adsorbed onto or incorporated within the coating surface (e.g. within any of its layers) without covalent linkage.

In medical devices, it may be appropriate to attach drug molecules to a hyperbranched polymer of the layered coating (e.g. a hyperbranched polymer of the outer coating layer) in addition to the anti-coagulant entity. In one embodiment, the linkage between the drug molecules and the coating is a degradable covalent linkage to allow migration (i.e. elution) of the drug molecules from the polymer surface. Alternatively, the drug may be adsorbed onto or incorporated within the coating surface without covalent linkage. The drugs may also be incorporated into the voids of the hyperbranched polymer prior to usage in the coating build up. Hydrophobic drugs may, in particular, be incorporated into the hydrophobic voids of the hyperbranched polymer. A specific application of this is in drug eluting stents. Exemplary drugs that may be used in this embodiment include drugs that prevent restenosis such as anti-angiogenic or anti-proliferative drugs such as paclitaxel and sirolimus. Another application is the use of elutable heparin or other anti-coagulant entities. In another embodiment an antimicrobial drug may be attached to the coating in addition to the anti-coagulant entity.

When beneficial agents are covalently attached to a molecule of the coating, this may be achieved by covalently attaching beneficial agent(s) to cationic hyperbranched polymer molecules as described herein through functional end groups which are not involved in attachment to the anti-coagulant entity. These functional end groups may be the original functionality (e.g. primary amine) or the functionality may be changed prior to attachment to the beneficial agent. The coupling of beneficial agents may be conducted in a similar manner, as earlier described, as for the coupling of anti-coagulant entities.

Beneficial agents may be coupled to hyperbranched polymers of the invention before coupling of anti-coagulant entities, however more usually they will be coupled afterwards.

More generally, the layered coating of the device (e.g. a medical device) may optionally comprise at least one beneficial agent selected from: paclitaxel, a taxane or other paclitaxel analogue; estrogen or estrogen derivatives; heparin or another thrombin inhibitor, hirudin, hirulog, apyrase, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; aspirin, ticlopidine or another antiplatelet agent; vascular endothelial growth factor (VEGF) or analogues thereof; colchicine or another antimitotic, or another microtubule inhibitor; cytochalasin or another actin inhibitor; a remodeling inhibitor; deoxyribonucleic acid, an antisense nucleotide or another agent for molecular genetic intervention; a cell cycle inhibitor (such as the protein product of the retinoblastoma tumor suppressor gene), or analogues thereof GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; prostaglandin, prostacyclin or analogues thereof; an immunosuppressive agent (such as cyclosporine or rapamycin (also known as sirolimus) and analogues thereof); an antimicrobial agent (e.g. compounds selected from the group consisting of diamidines, iodine and iodophors, peroxygens, phenols, bisphenols, halophenols, biguanides, silver compounds, triclosan, chlorhexidine, triclocarban, hexachlorophene, dibromopropamidine, chloroxylenol, phenol and cresol or combinations thereof) an antibiotic, erythromycin orvancomycin; dopamine, bromocriptine mesylate, pergolide mesylate or another dopamine agonist; or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor, ascorbic acid, alphatocopherol, superoxide dismutase, deferoxyamine, a 21-aminosteroid (lasaroid) or another free radical scavenger, iron chelator or antioxidant; angiopeptin; a $^{14}$C-, $^{3}$H-, $^{131}$I-, $^{32}$P or $^{36}$S-radiolabelled form or other radiolabelled form of any of the foregoing; or a mixture of any of these.

Further beneficial agents that may be incorporated into the surface of the device include lubricious agents including polymers such as hydrophilic or hydrogel polymers containing polar or charged functional groups which render them soluble in water. These agents incorporate polar groups that have an affinity to water molecules in solution, and are broadly classified as hydrogels. It may also be appropriate to attach lubricious agents to the coating in addition to the anti-coagulant entity. In one embodiment, the linkage between the lubricious agents and the outer coating layer may be a covalent linkage. Alternatively, the lubricious agent may be adsorbed ionically or physically onto or incorporated within the coating surface without covalent linkage. Examples of lubricous agents are, but are not limited to, hyaluronic acid, hyaluronic acid derivatives, poly-N-vinylpyrrolidone, poly-N-vinylpyrrolidone derivatives, polyethylene oxide, polyethylene oxide derivatives, polyethylene glycol, polyethylene glycol derivatives, polyvinylalcohol, polyvinylalcohol derivatives, polyacrylic acid, polyacrylic acid derivatives, silicon, silicon derivatives, polysaccharide, polysaccharide derivatives, Sulfonated polystyrene, Sulfonated polystyrene derivatives, polyallylamine, polyallylamine derivatives, polyethyleneimine, polyethyleneimine derivatives, polyoxazoline, polyoxazoline derivatives, polyamine, polyamine derivatives and combinations thereof. Such beneficial agents may, for example, be covalently attached to hyperbranched polymer molecules in the outer coating layer.

When a device has several surfaces, the beneficial agent(s) may be incorporated into which ever surface is appropriate to achieve the beneficial effect. For example the beneficial agent(s) may be incorporated into the surface of a tubular device on either or both of the luminal and abluminal sides. When more than one beneficial agent is incorporated, the different beneficial agents may be incorporated into the same surface, or part of the surface, or different surfaces or parts of the surface.

The devices of the invention may have one or more of the following advantages in at least some embodiments:

The amount of the entity coupled to the outer most layer may be controlled;

Both end-point (one point) attachment and multi-point attachment of the entity, e.g. heparin, can be achieved, although end point (especially reducing end point) attachment is preferred;

The length of the covalent connection (linker(s) and spacer(s)) between the entity and the hyperbranched polymer may be controlled;

Full length heparin may be used thus avoiding the cleavage of heparin and thus optimizing the use of heparin raw material;

Use of full-length heparin or heparin linked via a spacer may improve the bioactivity of the bound heparin;

A uniform distribution of the entity over the outer coating layer can be obtained;

A uniform coating may be obtained which will mask the intrinsic properties, for example lower the thromogenic properties, of a device irrespective of the material of its manufacture;

A coating may be obtained which is comparatively smooth and/or lubricious;

The bioavailability of the anti-coagulant entity can be controlled and improved;

A non-thrombogenic coating which does not leach heparin and therefore has long lifetime may be obtained;

A coating whose properties are preserved upon aging may be obtained;

A coating whose properties are preserved upon sterilization (e.g. with EO) may be obtained;

A self-healing coating may be obtained due to the possibility of reversible forming of ionic interactions between the layers;

The number of steps for coating preparation may be minimised by using pre-fabricated components;

A robust manufacturing process can be obtained by using pre-fabricated components;

A coating may be prepared in which a pre-prepared conjugate with covalently bound heparin may be used in the coating build up process;

The biocompatibility of the prepared coating may be enhanced;

A coating according to the present invention may reduce the need for systemic heparin, and reduce the likelihood of contact activation;

A medical device having a combination of lubricity and thromboresistance can be obtained which may be beneficial in certain applications e.g. neuro vascular applications;

A medical device having a combination of drug eluting properties and thromboresistance can be obtained which may be beneficial in certain applications e.g. drug eluting stents and drug eluting balloons;

A medical device having a combination of anti-inflammatory properties and thromboresistance can be obtained which may be beneficial in certain applications e.g. cardiovascular applications;

An analytical or separation device with improved binding capacity to biomolecules may be obtained; and An analytical or separation device with extended heparin activity life time may be obtained.

The invention is illustrated, but in no way limited, by the following Examples:

EXAMPLES

All Lupasol samples were purchased from BASF. Lupasol® WF (ethylene diamine core) has an average molecular weight of 25 kDa as determined from light scattering. Dextrane sulfate was purchased from pK Chemicals A/S (PKC) and PAMAM dendrimers (ethylene diamine core) were purchased from Sigma Aldrich and Dendritech. PAMAM-G6.0-$NH_2$ is a PAMAM dendrimer (6th generation) with molecular weight of approximately 60 kDa. PAMAM-G8.0-$NH_2$ is a PAMAM dendrimer (8th generation) with molecular weight of approximately 230 kDa. PPI G5 dendrimer (butane-1, 4-diamine core) was purchased from Aldrich. PPI G5 is a dendrimer ($5^{th}$ generation) with a molecular weight of approximately 7 kDa. The polyamine Epomin P-1050 (ethylene diamine core) was purchased from Nippon Shokubai and has an average molecular weight of 70 kDa. The polyamine G-35 was purchased from Wuhan Bright Chemicals and has an average molecular weight of 70 kDa. All polyamine stock solutions were 5 wt % in water. The dextran sulfate stock solution was 6 wt % in water. The solutions were subsequently diluted as appropriate before use. A water rinse was performed in between each process step as appropriate.

Example Headings

1. Preparation of underlayer
2. Preparation of a non-thrombogenic coating comprising a hyperbranched polymer in the outer coating layer
3. Preparation of a non-thrombogenic coating comprising a pre-prepared heparin functionalized hyperbranched polymer in the outer coating layer
4. Derivatized heparin entities
5. Derivatized hyperbranched polymers
6. Evaluation of heparin density and blood platelet loss
7. Preparation of intermediates
8. Preparation of a hydrophilic and lubricious coatings
9. Preparation of drug eluting coatings
10. Biocompatibility study
11. Hemo-compatibility of EO sterilized coatings comprising hyperbranched polymers

Example 1. Preparation of Underlayer

Example 1.1: Preparation of Underlayer Comprising Lupasol® SN

A PVC surface was pretreated using the method described by Larm et al in EP-B-0086186 and EP-495820 (layer-by-layer, polyelectrolyte charge interactions) ending with a layer of sulfated polysaccharide.

The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers ending with the sulfated polysaccharide.

Example 1.2: Preparation of Underlayer Comprising Lupasol®WF

A PVC surface was pretreated using the method described by Larm et al in EP-B-0086186 and EP-495820 (layer-by-layer; polyelectrolyte charge interactions) ending with a layer of sulfated polysaccharide.

The luminal surface of a PVC tubing (I.D. 3 mm) was cleaned with isopropanol and an oxidizing agent. The priming was built-up by alternated adsorption of a positively charged polyamine (Lupasol® WF, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers ending with the sulfated polysaccharide.

Example 1.3: Preparation of Underlayer Comprising PAMAM-G6.0-NH$_2$ Dendrimer Quartz Crystal Microbalance (QCM) crystals covered with gold (QSX 301, Q-Sense) were coated according to Example 1.1 using 5 wt % in MeOH PAMAM-G6.0-NH$_2$ (1 mL/L) to obtain a 3 bilayer coating consisting of alternatively layers of PAMAM-G6.0-NH$_2$ and a sulfated polysaccharide (6 wt % in water). The polyamine was crosslinked with a difunctional aldehyde (crotonaldehyde). A 2 min water rinse is conducted in between each adsorption step. The gold surface was primed with 3 bilayers ending with the sulfated polysaccharide.

Example 1.4: Preparation of Underlayer Comprising Lupasol® SK and Heparin Functionalized PAMAM-G6.0-NH$_2$ Dendrimer The luminal surface of a PVC tubing (I.D. 3 mm) was cleaned with isopropanol and an oxidizing agent. The priming was built-up by alternated adsorption of a positively charged polyamine (Lupasol® SK, 5 wt % in water, 10 minutes) and negatively charged PAMAM-heparin conjugate (400 mg/L, from Example 5.2, 20 minutes). The polyamine was crosslinked with a difunctional aldehyde (crotonaldehyde). Every pair of polyamine and PAMAM-heparin conjugate is called one bilayer. The PVC surface was primed with 3 bilayers ending with the PAMAM-heparin conjugate from Example 5.2.

Example 1.5: Preparation of Underlayer Using Lupasol® WF and Heparin Functionalized PAMAM-G6.0-NH$_2$ Dendrimer The luminal surface of a PVC tubing (I.D. 3 mm) was cleaned with isopropanol and an oxidizing agent. The priming was built-up by alternated adsorption of a positively charged polyamine (Lupasol® WF, 5 wt % in water, 10 minutes) and negatively charged PAMAM-heparin conjugate (400 mg/L, from Example 5.2, 20 minutes). The polyamine was crosslinked with a difunctional aldehyde (crotonaldehyde). Every pair of polyamine and PAMAM-heparin conjugate is called one bilayer. The PVC surface was primed with 3 bilayers ending with the PAMAM-heparin conjugate from Example 5.2.

Example 1.6: Preparation of Underlayer Comprising G-35

The luminal surface of a PVC tubing (I.D. 3 mm) was cleaned with isopropanol and an oxidizing agent. The priming was built-up by alternated adsorption of a positively charged polyamine (G-35, 5 wt % in water) and negatively charged sulfated polysaccharide (dextran sulfate, 6 wt % in water). The polyamine is crosslinked with a difunctional aldehyde (crotonaldehyde). Every pair of polyamine and sulfated polysaccharide is called one bilayer. The PVC surface was primed with 3 bilayers ending with the sulfated polysaccharide.

Example 1.7: Preparation of Underlying Layers Using Lupasol®SK

The luminal surface of a PVC tubing (I.D. 3 mm) was cleaned with isopropanol and an oxidizing agent. The priming was built-up by alternated adsorption of a positively charged polyamine (Lupasol® SK, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers ending with the sulfated polysaccharide.

Example 1.8: Preparation of Underlying Layers Using Epomin P-1050

The luminal surface of a PVC tubing (I.D. 3 mm) was cleaned with isopropanol and an oxidizing agent. The priming was built-up by alternated adsorption of a positively charged polyamine (Epomin P-1050, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers ending with the sulfated polysaccharide.

Example 2. Preparation of a Non-Thrombogenic Coating Comprising a Hyperbranched Polymer in the Outer Coating Layer

Example 2.1: Preparation of Outer Coating Layer Comprising Lupasol® WF on Underlayer Comprising Lupasol®SN A solution of Lupasol® WF (5 wt %) was allowed to adsorb for 10 minutes to the prefabricated coating surface from Example 1.1 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.2: Preparation of Outer Coating Layer Comprising Lupasol® WF on Underlayer Comprising Lupasol®WF A solution of Lupasol® WF (5 wt %) was allowed to adsorb for 10 minutes to the prefabricated coating surface from Example 1.2 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.3: Preparation of Outer Coating Layer Comprising PAMAM-G6.0-NH$_2$ Dendrimer on Underlayer Comprising Lupasol®SN A solution of PAMAM-G6.0-NH$_2$ (5 wt %) was allowed to adsorb for 10 minutes to the prefabricated coating surface from Example 1.1 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.4: Preparation of Outer Coating Layer Comprising PAMAM-G6.0-NH$_2$ Dendrimer on Underlayer Comprising PAMAM-G6.0-NH$_2$ Dendrimer A solution of PAMAM-G6.0-NH$_2$ (5 wt %) was allowed to adsorb for 30 minutes to the prefabricated coating surface from Example 1.3 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.5: Preparation of Outer Coating Layer Comprising G-35 on Underlayer Comprising Lupasol®SN A solution of G-35 (5 wt %) was allowed to adsorb for 10 minutes to the prefabricated coating surface from Example 1.1 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.6: Preparation of Outer Coating Layer Comprising G-35 on Underlayer Comprising G-35

A solution of G-35 (5 wt %) was allowed to adsorb for 10 minutes to the prefabricated coating surface from Example 1.6 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.7: Preparation of Outer Coating Layer Comprising 10 wt % Lupasol® WF and 90 Wt % Lupasol®SN on Underlayer Comprising Lupasol® SN A mixture of 10 wt % Lupasol® WF (5 wt % solution) and 90 wt % Lupasol® SN (5 wt % solution) was allowed to adsorb for 10 minutes to the prefabricated surface from Example 1.1 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.8: Preparation of Outer Coating Layer Comprising 10 wt % Lupasol® WF and 90 Wt % Lupasol® SK on Underlayer Comprising Lupasol® SK A mixture of 10 wt % Lupasol® WF (5 wt % solution) and 90 wt % Lupasol® SK (5 wt % solution) was allowed to adsorb for 10 minutes to the prefabricated coating surface from Example 1.7 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.9: Preparation of Outer Coating Layer Comprising Lupasol® WF on Underlayer Comprising Lupasol®SK A solution of Lupasol® WF (5 wt %) was allowed to adsorb for 10 minutes to the prefabricated coating surface from Example 1.7 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.10: Preparation of Outer Coating Layer Comprising Epomin P-1050 on Underlayer Comprising Lupasol®SN A solution of Epomin P-1050 (5 wt %) was allowed to adsorb for 10 minutes to the prefabricated coating surface from Example 1.1 followed by a 1 hour coupling step of nitrous acid degraded heparin (325 mg/L), from Example 4.1, using a reducing agent (sodium cyanoborohydride, 2.5 wt % in water). A 2 min water rinse is conducted in between each adsorption step. The fabricated non-thrombogenic coating was treated with a borate/phosphate solution to remove any potential ionically bound heparin prior to evaluation of its non-thrombogenic properties.

Example 2.11: Preparation of Outer Coating Layer Comprising Heparinized Lupasol®WF on Underlayer Comprising Lupasol®SN Lupasol® WF (5 wt % in water) was allowed to adsorb onto an underlaying layer described essentially as in Example 1.1 yielding a positively charged surface. Na heparin (325 mg/L) was subsequently coupled to the positively charged layer using 1-Ethyl-3-(3-dimethylaminopropyl) carbodiimide (EDC) (23.35 mg/L) at room temperature for 60 minutes followed by a borate/phosphate rinse to remove any loosely bound heparin prior to evaluation of the non-thrombogenic effect of the coating.

Example 2.12: Preparation of Outer Coating Layer Comprising Apyrase Functionalized Lupasol®WF on Underlayer Comprising Lupasol® SN Apyrase, ≥200 units/mg protein, derived from potato was purchased from Sigma-Aldrich. The carboxylic content in apyrase was calculated to be approximately 90 moles of COOH per 1 mole of apyrase based on an amino acid analysis performed by Aminosyraanalyscentralen, Sweden. Carboxylic groups in non-thrombogenic agents, such as apyrase, may be used to link them to an amine containing hyperbranched polymer using EDC, or EDC like, reagents essentially as described in Example 2.11.

Example 3. Preparation of a Non-Thrombogenic Coating Comprising a Pre-Prepared Heparin Functionalized Hyperbranched Polymer in the Outer Coating Layer

Example 3.1: Preparation of Outer Coating Layer Comprising Heparin Functionalized PAMAM-G6.0-NH$_2$ Dendrimer on Underlayer Comprising Lupasol® SN The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers and one layer of Lupasol® SN. Heparin functionalized PAMAM-G6.0-NH$_2$ dendrimer (150 mg/L) from Example 5.2 was deposited onto the positively charged Lupasol® SN coating for 1 hour followed by a borate/phosphate rinse to remove any loosely bound heparin conjugate prior to evaluation of the non-thrombogenic effect of the coating.

Example 3.2: Preparation of Outer Coating Layer Comprising Heparin Functionalized PAMAM-G6.0-NH$_2$ Dendrimer on Underlayer Comprising Lupasol®SK, Lupasol® WF and Heparin Functionalized PAMAM-G6.0-NH$_2$ Dendrimer The luminal surface of a PVC tubing (I.D. 3 mm) was cleaned with isopropanol and an oxidizing agent. The priming was built-up by alternated adsorption of a positively charged polyamine (Lupasol® SK, 5 wt % in water) and negatively charged PAMAM-heparin conjugate (400 mg/L, from Example 5.2). The polyamine was crosslinked with a difunctional aldehyde (crotonaldehyde). Every pair of polyamine and PAMAM-heparin conjugate is called one bilayer. The PVC surface was primed with 3 bilayers as just described (also, see Example 1.4) followed by one layer of Lupasol® WF. Heparin functionalized PAMAM-G6.0-NH$_2$ dendrimer (400 mg/L) from Example 5.2 was deposited onto the positively charged Lupasol®WF coating for 20 minutes followed by a water rinse to remove any loosely bound heparin conjugate prior to evaluation of the non-thrombogenic effect of the coating.

Example 3.3: Preparation of Outer Coating Layer Comprising Heparin Functionalized PAMAM-G6.0-NH$_2$ Dendrimer on Underlayer Comprising Lupasol®WF and Heparin Functionalized PAMAM-G6.0-NH$_2$ Dendrimer The luminal surface of a PVC tubing (I.D. 3 mm) was cleaned with isopropanol and an oxidizing agent. The priming was built-up by alternated adsorption of a positively charged polyamine (Lupasol® WF, 5 wt % in water) and negatively charged PAMAM-heparin conjugate (400 mg/L, from Example 5.2). The polyamine was crosslinked with a difunctional aldehyde (crotonaldehyde). Every pair of polyamine and PAMAM-heparin conjugate is called one bilayer. The PVC surface was primed with 3 bilayers as just described (also, see Example 1.5) followed by one layer of Lupasol® WF. Heparin functionalized PAMAM-G6.0-NH$_2$ dendrimer (400 mg/L) from Example 5.2 was deposited onto the positively charged Lupasol® WF coating for 20 minutes followed by a water rinse to remove any loosely bound heparin conjugate prior to evaluation of the non-thrombogenic effect of the coating.

Example 3.4: Preparation of Outer Coating Layer Comprising Heparin Functionalized PAMAM-G6.0-NH$_2$ Dendrimer on Underlayer Comprising Lupasol® SN The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers and one layer of Lupasol® SN. Heparin functionalized PAMAM-G6.0-NH$_2$ dendrimer (425 mg/L) from Example 5.2 was deposited onto the positively charged Lupasol® SN coating for 1 hour followed by a borate/phosphate rinse to remove any loosely bound heparin conjugate prior to evaluation of the non-thrombogenic effect of the coating.

Example 3.5: Preparation of Outer Coating Layer Comprising Heparin Functionalized Lupasol®WF on Underlayer Comprising Lupasol® SN The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers and one layer of Lupasol® SN. Heparin functionalized Lupasol® WF (425 mg/L) from Example 5.3 was deposited onto the positively charged Lupasol® SN coating for 1 hour followed by a borate/phosphate rinse to remove any loosely bound heparin conjugate prior to evaluation of the non-thrombogenic effect of the coating.

Example 3.6: Preparation of Outer Coating Layer Comprising Heparin Functionalized PAMAM-G8.0-NH$_2$ Dendrimer on Underlayer Comprising Lupasol® SN The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers and one layer of Lupasol® SN. Heparin functionalized PAMAM-G8.0-NH$_2$ dendrimer (425 mg/L) from Example 5.6 was deposited onto the positively charged Lupasol® SN coating for 1 hour followed by a borate/phosphate rinse to remove any loosely bound heparin conjugate prior to evaluation of the non-thrombogenic effect of the coating.

Example 3.7: Preparation of Outer Coating Layer Comprising Heparin Functionalized PPI G5 Dendrimer on Underlayer Comprising Lupasol® SN The luminal surface of a PVC tubing (I.D. 3 mm) was cleaned with isopropanol and an oxidizing agent. The priming was built-up by alternated adsorption of a positively charged polyamine (Lupasol® SN, 5 wt % in water) and negatively charged sulfated polysaccharide (dextran sulfate, 6 wt % in water). The polyamine was crosslinked with a difunctional aldehyde (crotonaldehyde). Every pair of polyamine and sulfated polysaccharide is called one bilayer. The PVC surface was primed with 3 bilayers and one layer of Lupasol® SN. Heparin functionalized PPI G5 dendrimer (425 mg/L) from Example 5.7 was deposited onto the positively charged Lupasol® SN coating for 1 hour followed by a borate/phosphate rinse to remove any loosely bound heparin conjugate prior to evaluation of the non-thrombogenic effect of the coating.

Example 4. Derivatized Heparin Entities

Example 4.1: Preparation of Aldehyde End-Point Functionalized Heparin

Aldehyde functionalized heparin is prepared essentially as in Example 2 of U.S. Pat. No. 4,613,665.

Example 4.2: Preparation of Thiol End-Point Functionalized Heparin

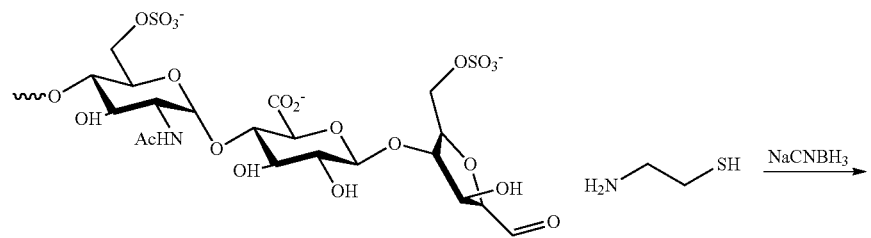

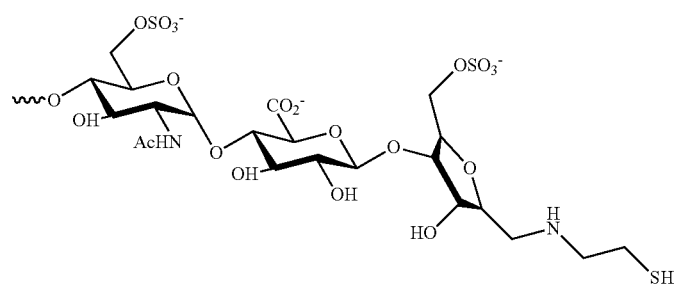

Nitrous acid degraded heparin with aldehyde groups (prepared essentially as in Example 2 of U.S. Pat. No. 4,613,665) (5.00 g, 1.0 mmol), cysteamine hydrochloride (0.57 g, 5.0 mmol) and sodium chloride (0.6 g) were dissolved in purified water. The pH was adjusted to 6.0 with 1 M NaOH (aq) and 1 M HCl (aq). To the solution was added 3.1 ml of 5% (aq) NaCNBH$_3$ (0.16 g, 2.5 mmol) and the reaction was stirred over night at room temperature. The pH was adjusted to 11.0 with 1 M NaOH (aq) and the resulting product was dialyzed against purified water with a SpectraPor dialysis membrane (MWCO 1 kD, flat width 45 mm) for three days. The reaction mixture was then concentrated and freeze dried to obtain 2.6 g of a white fluffy powder.

Example 4.3: Preparation of Alkyne End-Point Functionalized Heparin

Alkyne functionalized nitrous acid degraded heparin is prepared essentially as in Example 3a of WO2010/029189.

Example 4.4: Preparation of Alkyne End-Point Functionalized Native Heparin

Alkyne functionalized native heparin prepared essentially as in Example 3b of WO2010/029189.

Example 4.5: Preparation of Azide End-Point Functionalized Heparin and Azide Functionalized Native Heparin Azide functionalized nitrous acid degraded heparin and azide functionalized native heparin is prepared essentially as in Example 4 of WO2010/029189.

Example 5. Derivatized Hyperbranched Polymers

Example 5.1: Preparation of Alkene Functionalized PAMAM-G6.0-NH$_2$ Dendrimer A stock solution with 3.75 mg of NHS activated 5-hexenoic acid/mL MeOH was prepared. See Example 7.1 for preparation of NHS activated alkene.

2 mL of a 5 wt % PAMAM-G6.0-NH$_2$ solution in MeOH was added to 1 mL of the stock solution (3.75 mg of NHS activated 5-hexenoic acid) and 9 mL of MeOH (0° C.). The reaction was allowed to proceed over night. The solvent was evaporated using a rotary evaporator and a vacuum oven. High purity of the obtained material was confirmed by $^1$H and $^{13}$C NMR. A functionalization degree of 2% was obtained (5-6 alkenes/dendrimer)

Example 5.2: Preparation of Heparin Functionalized PAMAM-G6.0-NH$_2$ Dendrimer with Preserved Specific Activity

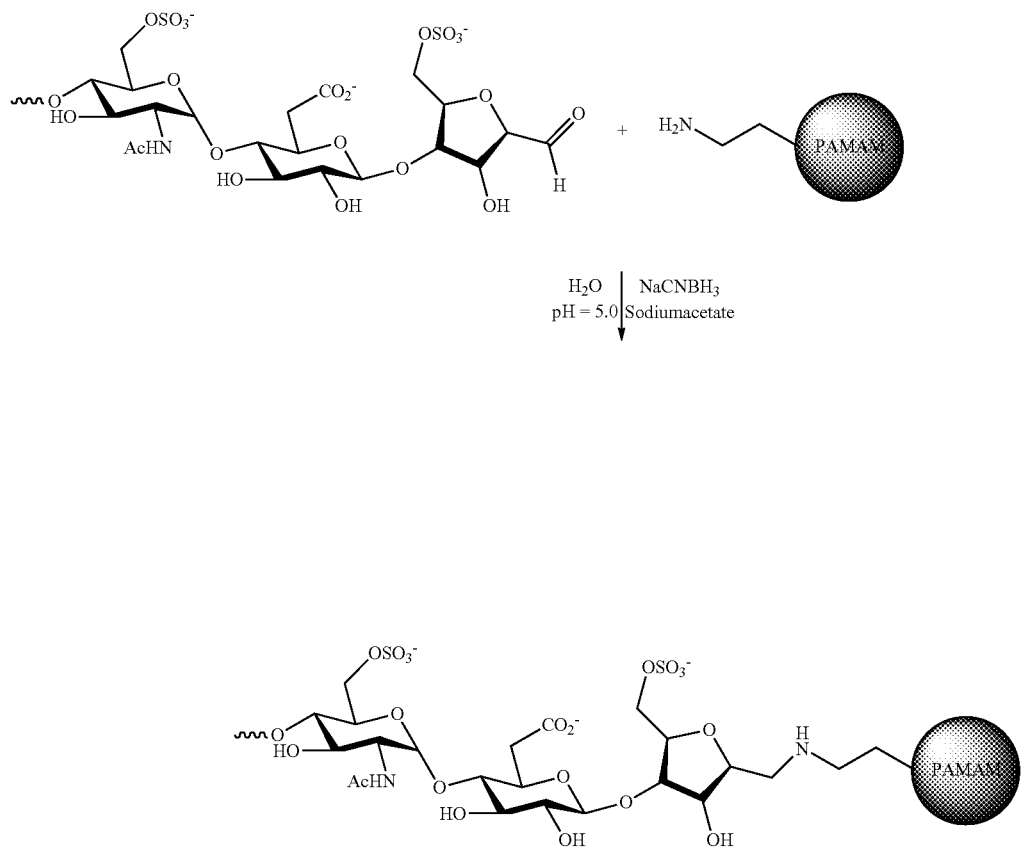

Aldehyde end-point functionalized heparin, from Example 4.1, (5.0 g, 0.56 mmol) was dissolved in 15 mL acetate buffer (pH=5.0) under vigorously stirring. 2 mL of a 5 wt % solution of PAMAM-G6.0-NH$_2$ dendrimer (ethylene diamine core) (80.6 mg, 1.39 mol) in MeOH was added to the heparin solution followed by addition of 10 mL sodium cyanoborohydride (2.5 wt % in H$_2$O). The solution was left to stir in the fume hood over night at room temperature. The solution was transferred to a dialysis bag (MWCO 50,000 Da) and dialyzed thoroughly. The content of the dialysis bag was thereafter transferred to a round bottom flask and lyophilized over night. The dry weight of the content in the flask was 830 mg (~60 heparin chains/PAMAM-G6.0-NH$_2$ dendrimer or 23% functionalization of the primary amines in PAMAM-G6.0-NH$_2$). The specific activity of the PAMAM bound heparin in the conjugate was determined to be >100 IU/mg. The heparin used for the preparation, prior to coupling, has a specific activity of approximately 100 IU/mg.

Example 5.3: Preparation of Heparin Functionalized Lupasol® WF with Preserved Specific Activity Heparin functionalized Lupasol®WF was prepared essentially as described in Example 5:2.

Example 5.4: Preparation of Azide Functionalized Lupasol® WF

Azide functionalized Lupasol® WF can be prepared essentially as described for Lupasol® SN in Example 2a of WO2010/029189

Example 5.5: Preparation of Alkyne Functionalized Lupasol®WF

Alkyne functionalized Lupasol® WF can be prepared essentially as described for Lupasol® SN in Example 2b of WO2010/029189

Example 5.6: Preparation of Heparin Functionalized PAMAM-G8.0-NH$_2$ Dendrimer with Preserved Specific Activity Heparin functionalized PAMAM-G8.0-NH$_2$ was prepared essentially as described in Example 5:2.

Example 5.7: Preparation of Heparin Functionalized PPI G5 Dendrimer with Preserved Specific Activity Heparin functionalized PPI G5 dendrimer was prepared essentially as described in Example 5:2.

Example 5.8: Preparation of Functionalized Hyperbranched Polymers

Hyperbranched polymers with chemical groups, or functionalities, selected from Table 3 (Func. group 1 and Func. group 2) may be prepared by a person skilled in the art.

Non-thrombogenic entities (e.g. heparin) with chemical groups, or functionalities, selected from Table 3 (Func. 1 and Func. 2) may be prepared by a person skilled in the art.

The functionalized hyperbranched polymers may be reacted with a functionalized non-thrombogenic entity (e.g. heparin) by a person skilled in the art to yield a hyperbranched polymer derivatised with a non-thromogenic entity (e.g. heparin).

Example 6. Evaluation of Heparin Density and Blood Platelet Loss

Heparin Density Test (for Measurement of the Heparin Content in the Coating)

Quantification of surface immobilized heparin was performed essentially as described in Smith R. L. and Gilkerson E (1979), *Anal. Biochem.*, 98, 478-480.

Toluidine Blue Staining Test (for Evaluation of Heparin Distribution)

Figure 9:
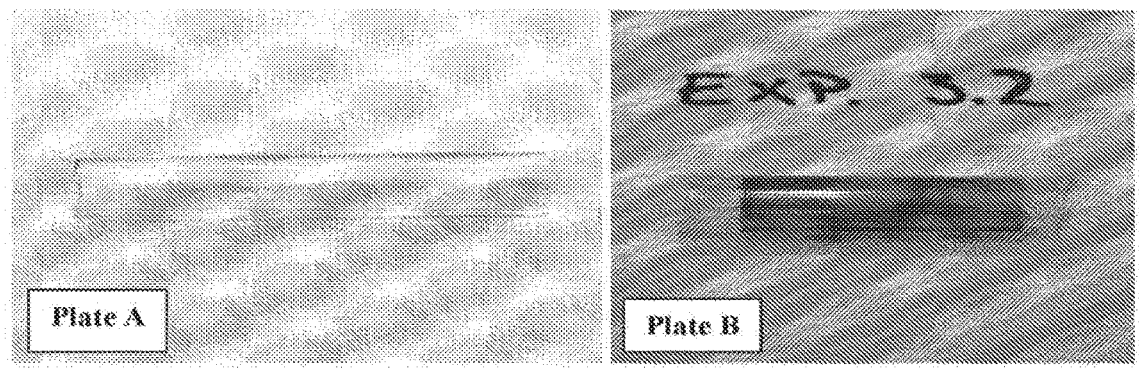
FIG. 9 shows an exemplary Toluidine blue staining of a PVC tube before and after coated with a heparin-containing coating according to the invention (see Example 3.2 and Example 6.3).
Figure 10:
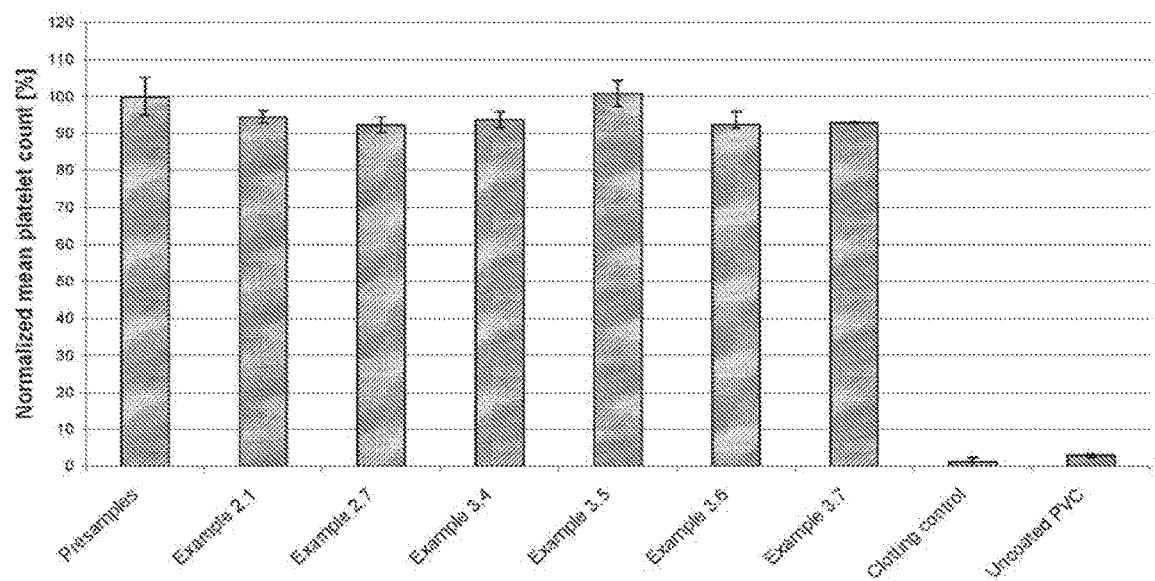
FIG. 10 shows the percentage of platelets remaining in blood after contact with various non-thrombogenic coatings (see Example 11).

Heparin distribution is evaluated using Toluidine blue staining solutions. The solution was prepared by dissolving 200 mg of Toluidine blue in 1 L of water. The samples were subjected to the staining solution for 2 minutes prior to extensive water rinse. A blue/violet staining indicates that negatively charged heparin molecules are homogenously distributed in the outer coating layer as exemplified by FIG. 9 plate B.

Blood Loop Evaluation Test (for Measurement of Platelet Loss).

Blood loop evaluation was performed on samples, as coated, to show the preserved heparin bioactivity of the non-thrombogenic surface. First the luminal side of the coated tubing was washed with 0.15 M NaCl for 15 hours at a flow of 1 mL/min to ensure that all loosely bound heparin was rinsed off and a stable surface remains. Then the washed tubings were incubated in a Chandler loop model performed essentially according to Andersson et al. (Andersson, J.; Sanchez, J.; Ekdahl, K. N.; Elgue, G.; Nilsson, B.; Larsson, R. J Biomed Mater Res A 2003, 67(2), 458-466) at 20 rpm. The platelets, from fresh blood and from the blood collected from the loops, were counted in a cell counter to measure the loss of platelets which indicates thrombosis.

Example 6.1: Coating Properties in Terms of Heparin Density and Platelet Loss, after Blood Exposure, of the Non-Thrombogenic Surface

| Example No. | Polyamine in underlayer | Neg. charged polymer in underlayer | Hyperbranched polymer in outer coating layer | Heparin density$^a$ [µg/cm$^2$] | Toluidine blue staining$^b$ | Platelets loss [%] |
|---|---|---|---|---|---|---|
| 1.1 | Lupasol ® SN | PS* | N/A** | N/A** | No | N/A** |
| 1.2 | Lupasol ® WF | PS* | N/A** | N/A** | No | N/A** |
| 2.1 | Lupasol ® SN | PS* | Lupasol ® WF | 4.7 | Yes | 0 |
| 2.2 | Lupasol ® WF | PS* | Lupasol ® WF | 5.3 | Yes | 0 |
| 2.3 | Lupasol ® SN | PS* | PAMAM-G6.0-NH$_2$ | 1.4 | Yes | 8 |
| 2.4 | PAMAM-G6.0-NH$_2$ | PS* | PAMAM-G6.0-NH$_2$ | 5.1 | Yes | N/T*** |
| 2.5 | Lupasol ® SN | PS* | G-35 [70 kDa] | 7.6 | Yes | 0 |

-continued

| Example No. | Polyamine in underlayer | Neg. charged polymer in underlayer | Hyperbranched polymer in outer coating layer | Heparin density$^a$ [μg/cm$^2$] | Toluidine blue staining$^b$ | Platelets loss [%] |
|---|---|---|---|---|---|---|
| 2.6 | G-35 [70 kDa] | PS* | G-35 [70 kDa] | 3.9 | Yes | 1 |
| 2.7 | Lupasol ® SN | PS* | Lupasol ® WF | 5.5 | Yes | N/T** |
| 2.8 | Lupasol ® SK | PS* | Lupasol ® WF | 3.5 | Yes | 3 |
| 2.9 | Lupasol ® SK | PS* | Lupasol ® WF | 8.6 | Yes | 1 |
| 2.10 | Lupasol ® SN | PS* | Epomin P-1050 | 8.4 | Yes | N/T*** |
| 2.11 | Lupasol ® SN | PS* | Lupasol ® WF | 5.1 | Yes | 0 |
| 3.1 | Lupasol ® SN | PS* | PAMAM-G6.0-NH$_2^c$ | 0.6 | Yes | 5 |
| 3.2 | Lupasol ® SK and Lupasol ® WF | PAMAM-G6.0-NH$_2^c$ | PAMAM-G6.0-NH$_2^c$ | 3.8 | Yes | 1 |
| 3.3 | Lupasol ® WF | PAMAM-G6.0-NH$_2^c$ | PAMAM-G6.0-NH$_2^c$ | 4.0 | Yes | 1 |
| 3.4 | Lupasol ® SN | PS* | PAMAM-G6.0-NH$_2^c$ | 0.9 | Yes | 14 |
| 3.5 | Lupasol ® SN | PS* | Lupasol WF$^c$ | 3.5 | Yes | 7 |
| 3.6 | Lupasol ® SN | PS* | PAMAM-G8.0-NH$_2^c$ | 0.6 | Yes | 12 |
| 3.7 | Lupasol ® SN | PS* | PPI G5$^c$ | 1.7 | Yes | 15 |
| Uncoated PVC | **N/A | **N/A | **N/A | **N/A | No | 94 |
| Clotting control | **N/A | *PS | **N/A | **N/A | ***N/T | 95 |

$^a$Mean out of 2 values
$^b$Yes means blue/violet staining. No means no staining at all
$^c$Deposition of pre-prepared heparin hyperbranched conjugate
*PS = Polysaccharide
**N/A = Not applicable
***N/T = Not tested The number of platelets present after the blood was exposed to the non-thrombogenic surface coating was calculated as a percentage of the number of platelets present before the blood was exposed to the non-thrombogenic surface coating and is presented graphically for various samples in FIG. 8.

Figure 8:
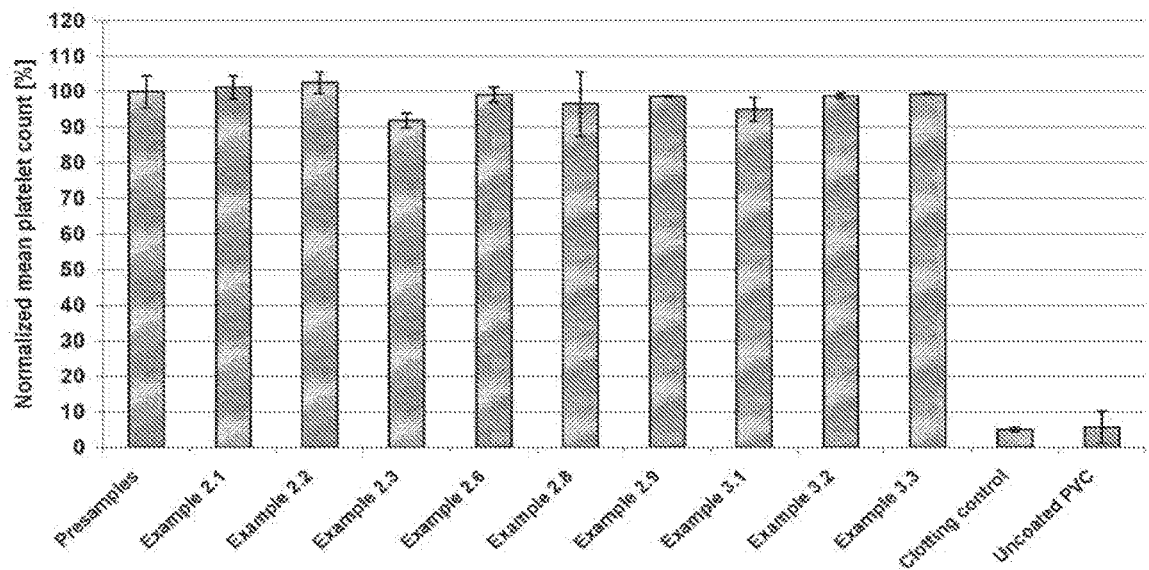
FIG. 8 shows the percentage of platelets remaining in blood after contact with various non-thrombogenic coatings (see Example 6).

As seen in the table above and in FIG. 8, there is virtually no platelet loss (platelet loss indicates thrombosis) seen for the heparin containing coatings tested. The uncoated PVC tubing and the surface with an outer layer of a sulfated polysaccharides ("clotting control") show significant thrombosis in this experiment.

Example 6.2: Staining of a Non-Thrombogenic Surface Using Toluidine Blue

Tubing from Example 2.2 was subjected to Toluidine blue stain solution (200 mg/L in water) by immersing in the solution for 2 minutes followed by extensive water rinse. A blue/violet color was observed on the surface of the luminal surface of the tubing indicating the covalent attachment of end-point functionalized heparin.

Example 6.3: Staining of a Non-Thrombogenic Surface Using Toluidine Blue

Tubing from Example 3.2 was subjected to Toluidine blue stain solution (200 mg/L in water) by immersing in the solution for 2 minutes followed by extensive water rinse. A blue/violet color was observed on the surface of the luminal surface of the tubing indicating the covalent attachment of end-point functionalized heparin in the PAMAM-heparin conjugate. The staining of the luminal surface of the PVC-tubing can be seen in FIG. 9.

Example 6.4: Staining of a Non-Thrombogenic Surface Using Toluidine Blue

Tubing from Example 3.3 was subjected to Toluidine blue stain solution (200 mg/L in water) by immersing in the solution for 2 minutes followed by extensive water rinse. A blue/violet color was observed on the surface of the luminal surface of the tubing indicating the covalent attachment of end-point functionalized heparin in the PAMAM-heparin conjugate.

Example 7. Preparation of Intermediates

Example 7.1: Synthesis of NHS-Activated 5-Hexenoic Acid

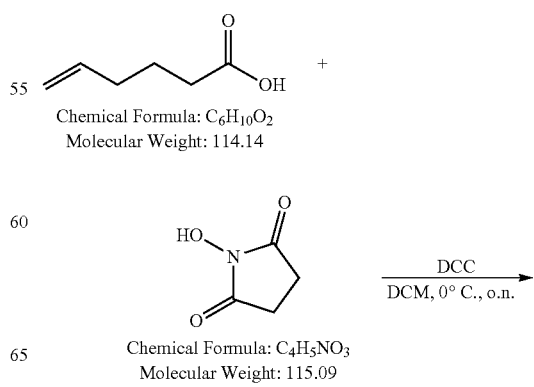

Chemical Formula: C$_6$H$_{10}$O$_2$
Molecular Weight: 114.14

Chemical Formula: C$_4$H$_5$NO$_3$
Molecular Weight: 115.09

DCC
DCM, 0° C., o.n.

-continued

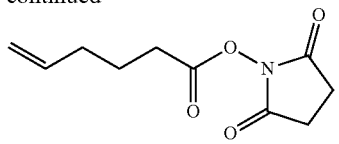

Chemical Formula: $C_{10}H_{13}NO_4$
Molecular Weight: 211.21

Hexenoic acid (1.00 g, 8.76 mmol) and hydroxysuccinimide (1.01 g, 8.76 mmol) was dissolved in 10 mL of DCM and stirred at 0° C. A solution of DCC (1.81 g, 8.76 mmol) in DCM (3 mL) was slowly added dropwise to the reaction mixture at 0° C. The reaction was left to stir over night where after the byproducts were filtered off and the remaining solution was concentrated using a rotor evaporator and dried under vacuum in oven. High purity of the obtained material was confirmed by $^1$H and $^{13}$C NMR.

Example 8. Preparation of a Hydrophilic and Lubricious Coatings

Example 8.1: A Hydrophilic and Lubricious Coating Comprising Lupasol®SK and Lupasol® WF QCM crystals were coated according to Example 1.7 using Lupasol® SK to obtain a 3 bilayer coating consisting of alternatively layers of Lupasol® SK and a sulfated polysaccharide. A layer of Lupasol® WF was subsequently adsorbed to the sulfated polysaccharide in order to obtain a coating with a cationic hyperbranched polymer as the outermost layer. A 2 min water rinse was conducted in between each adsorption step. These coatings were analyzed using contact angle (CA) measurements. A static CA of 53.0° (mean out of two samples) revealed that a hydrophilic and lubricious coating was obtained.

Example 8.2: A Hydrophilic and Lubricious Containing Coating Comprising Lupasol® SK, Lupasol®WF and Heparin QCM crystals were coated according to Example 1.7 using Lupasol® SK to obtain a 3 bilayer coating consisting of alternatively layers of Lupasol® SK and a sulfated polysaccharide. A layer of Lupasol® WF was subsequently adsorbed to the sulfated polysaccharide followed by a 1 hour coupling step of nitrous degraded heparin (325 mg/L), from Example 4.1, using a reducing agent (sodium cyanoborohydride, 2.5 wt % in water). A 2 min water rinse was conducted in between each adsorption step. The fabricated lubricious coating was treated with a borate/phosphate solution to remove any potential ionically bound heparin prior to evaluation using contact angle (CA) measurements. A static CA of 23.5° (mean out of two samples) reveled that a hydrophilic and lubricious coating was obtained.

Example 9. Preparation of Drug Eluting Coatings

Example 9.1: Incorporation of Doxorubicin into a Heparinized Coating

Doxorubicin was incorporated into a coating on a QCM crystal, prepared essentially as Example 2.3, by placing the QCM crystal in a water solution of doxorubicin (1 mg/25 mL of water). The loading step was followed by careful rinsing of the drug loaded coating using water prior to fluorescent evaluation of the coating. The crystal was dried in a vacuum oven prior to fluorescent evaluation. A strong red fluorescence could be detected indicating that doxorubicin was successfully incorporated into the coating.

Example 9.2: Incorporation of Doxorubicin and the Subsequent Release from a Coating Comprising Heparinized PAMAM-G6.0-NH$_2$ Dendrimer, Lupasol® SK and Lupasol® WF Doxorubicin was incorporated into a coating on a QCM crystal, prepared essentially as Example 3.2, by placing the QCM crystal in a water solution of doxorubicin (1 mg/25 mL of water). The loading step was followed by careful rinsing of the drug loaded coating using water prior to fluorescent evaluation of the coating. The crystal was dried in a vacuum oven prior to fluorescent evaluation. A strong red fluorescence could be detected indicating that doxorubicin was successfully incorporated into the coating. The drug loaded coating was subjected to a 2M NaCl-solution and a final water rinse followed by drying in vacuum oven prior to an additional fluorescent microscopy evaluation. The lack of red fluorescence indicates that the doxorubicin had eluted out from the coating.

Example 9.3: Incorporation of Doxorubicin and the Subsequent Release from a Coating Comprising Heparinized PAMAM-G6.0-NH$_2$ Dendrimer and Lupasol® WF Doxorubicin may be incorporated into a QCM crystal, prepared essentially as Example 3.3, by placing the QCM crystal in a water solution of doxorubicin (1 mg/25 mL of water) followed by careful rinsing of the drug loaded coating using water prior to fluorescent evaluation of the coating. A strong red fluorescence indicates that doxorubicin was successfully incorporated into the coating. The drug loaded coating was subjected to a 2M NaCl-solution followed by drying in vacuum oven prior to an additional fluorescent microscopy evaluation. The lack of red fluorescence indicated that the doxorubicin had been eluted out from the coating.

Example 10: Biocompatibility Study

Preparation of a biocompatible surface on a HDPE (High Density Poly Ethylene) HDPE sheets (30 cm$^2$, USP reference standard) were cleaned with isopropanol and an oxidising method. The sheets were then primed as in Example 1 with 3 bilayers ending with sulfated polysaccharide. The priming layers were reacted as in Example 2 with a hyperbranched polyamine followed by a coupling step where functionalized heparin was attached or as in Example 3 first with a polyamine layer followed by a heparin functionalized hyperbranched polymer with net negative charge. The coating was performed by immersing the materials into the coating solutions. The coatings were found to be non-toxic in a cytotoxicity testing using the Minimal Essential Medium (MEM) elution test as described in ISO10993 (see Example 10.1).

These results demonstrate the non-toxic biocompatible properties of the evaluated surface.

Example 10.1: Table of Biocompatibility

| Example No. | Polyamine in underlayer | Neg. charged polymer in underlayer | Hyperbranched polymer in outer coating layer | Passed | Not passed |
|---|---|---|---|---|---|
| 2.2 | Lupasol ® WF | PS* | Lupasol ® WF | Yes | |
| 3.6 | Lupasol ® SN | PS* | PAMAM-G8.0-NH$_2$[a] | Yes | |
| 3.7 | Lupasol ® SN | PS* | PPI G5[a] | Yes | |

*PS = Polysaccharide
[a]Deposition of pro-prepared heparin hyperbranched conjugate

Example 11: Hemo-Compatibility of EO Sterilized Coatings Comprising Hyperbranched Polymers EO Sterilization Differently coated substrates with a heparin functionalized hyperbranched polymer in the outer coating layer prepared as described in Examples 2 or 3 were subjected to sterilization by exposure to ethylene oxide (EO). The EO-sterilization was performed using a standard sterilization process used for medical devices.

Blood Loop Evaluation Test (for Measurement of Platelet Loss)

The EO-sterilized and washed tubings were incubated in a Chandler loop model performed essentially according to Andersson et al. (Andersson, J.; Sanchez, J.; Ekdahl, K. N.; Elgue, G.; Nilsson, B.; Larsson, R. J Biomed Mater Res A 2003, 67(2), 458-466), see Example 6. As seen in the table below there is virtually no platelet loss (platelet loss indicates thrombosis) seen for the EO sterilized heparin coatings prepared using the hyperbranched heparin conjugates prepared according to example 2 and 3. The uncoated PVC tubing and the clotting control (surface with an outer layer of sulfated polysaccharides not binding antithrombin) show significant thrombosis in this experiment.

Example 11.1 Presentation of Coating Stability in Terms of Blood Platelet Loss after EO Sterilization

| Example No. | Polyamine in underlayer | Neg. charged polymer in underlayer | Hyperbranched polymer in outer coating layer | Platelets loss [%] Pre EO-sterilization | Platelets less [%] Post EO-sterilization |
|---|---|---|---|---|---|
| 2.1 | Lupasol ® SN | PS* | Lupasol ® WF | 0 | 6 |
| 2.7 | Lupasol ® SN | PS* | Lupasol ® WF | N/T** | 8 |
| 3.4 | Lupasol ® SN | PS* | PAMAM-G6.0-NH$_2$[a] | 14 | 6 |
| 3.5 | Lupasol ® SN | PS* | Lupasol WF[a] | 7 | 0 |
| 3.6 | Lupasol ® SN | PS* | PAMAM-G8.0-NH$_2$[a] | 12 | 8 |
| 3.7 | Lupasol ® SN | PS* | PPI G5[a] | 15 | 7 |
| Uncoated PVC | N/A*** | N/A*** | N/A*** | 97 | N/T** |
| Clotting control | N/A*** | N/A*** | N/A*** | 96 | N/T** |

*PS = Polysaccharide
**N/T = Not tested
***N/A = Not applicable
[a]Deposition of pre-prepared heparin hyperbranched conjugate These results demonstrate that the non-thrombogenic properties of the stable surfaces prepared according to the invention are retained in spite of exposure to rigorous sterilization conditions.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and suitable and more suitable groups and embodiments of groups recited above.

The invention claimed is:

1. A non-thrombogenic device having a surface comprising a layered coating comprising an outer coating layer and an inner coating layer, wherein the outer coating layer comprises a plurality of cationic hyperbranched polymer molecules characterized by having:
   (i) a core moiety having a core moiety molecular weight of 14 to 1,000 Da;
   (ii) a total molecular weight of 1,500 to 1,000,000 Da;
   (iii) a ratio of the total molecular weight to the core moiety molecular weight of at least 80:1; and
   (iv) a plurality of functional end groups, whereby one or more of said functional end groups have an anti-coagulant entity covalently attached thereto,
   wherein the anti-coagulant entity is a heparin moiety, which is prepared by a process comprising, in order:
   (a) reacting a plurality of functional end groups of the hyperbranched polymer molecules with anti-coagulant entities such that each hyperbranched polymer molecule is covalently linked to a plurality of anti-coagulant entities;
   (b) attaching the hyperbranched polymer molecules to the outer coating layer; and
   (c) subjecting the device to ethylene oxide sterilization;
   wherein step (a) is carried out in solution,
   wherein the hyperbranched polymer is a dendrimer.

2. A device according to claim 1, wherein the heparin moiety is a full length (native) heparin moiety.

3. A device according to claim 1, wherein the heparin moiety is single point attached to each of the cationic hyperbranched polymer molecules.

4. A device according to claim 1, wherein the heparin moiety is attached to each of the cationic hyperbranched polymer molecules via a reducing end of the heparin moiety.

5. A device according to claim 1, wherein the functional end groups are primary amine groups.

6. A device according to claim 1, wherein the core moiety molecular weight is 50 to 130 Da.

7. A device according to claim 1, wherein the dendrimer is a polyamidoamine (PAMAM) dendrimer.

8. A device according to claim 1, wherein the total molecular weight of the hyperbranched polymer is 25,000 to 200,000 Da.

9. A device according to claim 1, wherein the ratio of the total molecular weight to the core moiety molecular weight is at least 100:1.

10. A device according to claim 1, wherein each of the anti-coagulant entities is covalently attached to the hyperbranched polymer molecule via a linker comprising:
    i. a secondary amine linkage;
    ii. an amide linkage;
    iii. a thioether linkage; or
    vi. a 1,2,3-triazole linkage.

11. A non-thrombogenic device having a surface comprising a layered coating comprising an outer coating layer and an inner coating layer, wherein the outer coating layer comprises a plurality of cationic hyperbranched polymer molecules characterized by having:
    (i) a core moiety having a core moiety molecular weight of 14 to 1,000 Da;
    (ii) a total molecular weight of 1,500 to 1,000,000 Da;
    (iii) a ratio of the total molecular weight to the core moiety molecular weight of at least 80:1; and
    (iv) a plurality of functional end groups, whereby one or more of said functional end groups have an anti-coagulant entity covalently attached thereto,
wherein the anti-coagulant entity is a heparin moiety, which is prepared by a process comprising, in order:
    (a) reacting a plurality of functional end groups of the hyperbranched polymer molecules with anti-coagulant entities such that each hyperbranched polymer molecule is covalently linked to a plurality of anti-coagulant entities;
    (b) attaching the hyperbranched polymer molecules to the outer coating layer; and
    (c) subjecting the device to ethylene oxide sterilization;
wherein step (a) is carried out in solution,
wherein the hyperbranched polymer is selected from polyamidoamine, polypropyleneimine, polyethyleneimine and polyaminepolymers and copolymers comprising one or more of polyamidoamine, polypropyleneimine, polyethyleneimine and polyamine hyperbranched polymers.

12. A device according to claim 11, wherein the heparin moiety is a full length (native) heparin moiety.

13. A device according to claim 11, wherein the heparin moiety is single point attached to each of the cationic hyperbranched polymer molecules.

14. A device according to claim 11, wherein the heparin moiety is attached to each of the cationic hyperbranched polymer molecules via a reducing end of the heparin moiety.

15. A device according to claim 11 wherein the hyperbranched polymer is a polyethyleneimine.

16. A device according to claim 11, wherein the functional end groups are primary amine groups.

17. A device according to claim 11, wherein the core moiety molecular weight is 50 to 130 Da.

18. A device according to claim 11, wherein the total molecular weight of the hyperbranched polymer is 25,000 to 200,000 Da.

19. A device according to claim 11, wherein the ratio of the total molecular weight to the core moiety molecular weight is at least 100:1.

20. A device according to claim 11, wherein each of the anti-coagulant entities is covalently attached to the hyperbranched polymer molecule via a linker comprising:
    i. a secondary amine linkage;
    ii. an amide linkage;
    iii. a thioether linkage; or
    vi. a 1,2,3-triazole linkage.

* * * * *